United States Patent
Frenkel et al.

(10) Patent No.: US 8,975,279 B2
(45) Date of Patent: Mar. 10, 2015

(54) AMINE SALTS OF LAQUINIMOD

(71) Applicants: Anton Frenkel, Netanya (IL); Avital Laxer, Tel Aviv (IL); Judith Aronheim, Rehovot (IL)

(72) Inventors: Anton Frenkel, Netanya (IL); Avital Laxer, Tel Aviv (IL); Judith Aronheim, Rehovot (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 0 days.

(21) Appl. No.: 14/068,599

(22) Filed: Oct. 31, 2013

(65) Prior Publication Data

US 2014/0128430 A1 May 8, 2014

Related U.S. Application Data

(60) Provisional application No. 61/723,495, filed on Nov. 7, 2012.

(51) Int. Cl.
| | |
|---|---|
| C12Q 1/68 | (2006.01) |
| C07D 215/56 | (2006.01) |
| C07C 215/08 | (2006.01) |
| C07C 215/10 | (2006.01) |
| C07C 229/26 | (2006.01) |

(52) U.S. Cl.
CPC ............ *C07D 215/56* (2013.01); *C07C 215/08* (2013.01); *C07C 215/10* (2013.01); *C07C 229/26* (2013.01)
USPC .......................................................... 514/312

(58) Field of Classification Search
None
See application file for complete search history.

(56) References Cited

U.S. PATENT DOCUMENTS

| | | | |
|---|---|---|---|
| 3,024,257 A | 3/1962 | Millar at al. | |
| 4,107,310 A | 8/1978 | Allais et al. | |
| 4,547,511 A | 10/1985 | Eriksoo et al. | |
| 4,628,053 A | 12/1986 | Fries et al. | |
| 4,738,971 A | 4/1988 | Eriksoo et al. | |
| 4,782,155 A | 11/1988 | Nakagawa et al. | |
| 5,139,878 A | 8/1992 | Kim et al. | |
| 5,716,638 A | 2/1998 | Touitou | |
| 5,912,349 A | 6/1999 | Sih | |
| 6,077,851 A | 6/2000 | Bjork et al. | |
| 6,121,287 A | 9/2000 | Bjork et al. | |
| 6,133,285 A | 10/2000 | Bjork et al. | |
| 6,307,050 B1 | 10/2001 | Kwiatkowski et al. | |
| 6,395,750 B1 | 5/2002 | Hellund et al. | |
| 6,593,343 B2 | 7/2003 | Bjork et al. | |

(Continued)

FOREIGN PATENT DOCUMENTS

| | | |
|---|---|---|
| EP | 0497740 | 12/1994 |
| EP | 1073639 | 2/2001 |

(Continued)

OTHER PUBLICATIONS

Comi, et al, New England Journal of Medicine, 366:1000-9, Mar. 15, 2012.*

(Continued)

*Primary Examiner* — San-Ming Hui
*Assistant Examiner* — Jeanmarie Calvillo
(74) *Attorney, Agent, or Firm* — John P. White; Gary J. Gershik; Cooper & Dunham LLP

(57) ABSTRACT

The subject invention provides a Laquinimod amine salt, which is laquinimod meglumine, laquinimod choline hydroxide, laquinimod L-lysine or laquinimod monoethanolamine.

20 Claims, 13 Drawing Sheets

(56) References Cited

U.S. PATENT DOCUMENTS

| | | |
|---|---|---|
| 6,605,616 B1 | 8/2003 | Bjork et al. |
| 6,613,574 B2 | 9/2003 | Shimada |
| 6,706,733 B2 | 3/2004 | Kimura et al. |
| 6,802,422 B2 | 10/2004 | Kalvelage et al. |
| 6,875,869 B2 | 4/2005 | Jansson |
| 7,560,557 B2 | 7/2009 | Jansson |
| 7,589,208 B2 | 9/2009 | Jansson et al. |
| 7,790,197 B2 | 9/2010 | Fergione et al. |
| 7,884,208 B2 | 2/2011 | Frenkel et al. |
| 7,989,473 B2 | 8/2011 | Patashnik et al. |
| 8,178,127 B2 | 5/2012 | Safadi et al. |
| 8,252,933 B2 | 8/2012 | Gant et al. |
| 8,314,124 B2 | 11/2012 | Jansson et al. |
| 8,383,645 B2 | 2/2013 | Patashnik |
| 2002/0173520 A1 | 11/2002 | Bjork et al. |
| 2003/0119826 A1 | 6/2003 | Manning et al. |
| 2003/0124187 A1 | 7/2003 | Mention et al. |
| 2004/0253305 A1 | 12/2004 | Luner et al. |
| 2005/0192315 A1 | 9/2005 | Jansson et al. |
| 2005/0215586 A1 | 9/2005 | Jansson et al. |
| 2005/0271717 A1 | 12/2005 | Berchielli et al. |
| 2007/0218062 A1 | 9/2007 | Bryan |
| 2007/0280891 A1 | 12/2007 | Tamarkin et al. |
| 2010/0158903 A1 | 6/2010 | Smith et al. |
| 2010/0209506 A1 | 8/2010 | Eisenrich |
| 2010/0260716 A1 | 10/2010 | Stohr et al. |
| 2010/0260755 A1 | 10/2010 | Gammans et al. |
| 2010/0310547 A1 | 12/2010 | Soliven |
| 2010/0322900 A1 | 12/2010 | Tarcic et al. |
| 2011/0027219 A1 | 2/2011 | Tarcic et al. |
| 2011/0034508 A1 | 2/2011 | Hayardeny et al. |
| 2011/0112141 A1 | 5/2011 | Frenkel et al. |
| 2011/0118308 A1 | 5/2011 | Frenkel et al. |
| 2011/0171270 A1 | 7/2011 | Dixit et al. |
| 2011/0217295 A1 | 9/2011 | Haviv et al. |
| 2011/0218203 A1 | 9/2011 | Kaye et al. |
| 2011/0251235 A1* | 10/2011 | Patashnik et al. ............. 514/312 |
| 2012/0010238 A1 | 1/2012 | Piryatinsky |
| 2012/0010239 A1 | 1/2012 | Fristedt |
| 2012/0142730 A1 | 6/2012 | Tarcic et al. |
| 2012/0142748 A1 | 6/2012 | Muthuppalaniappan et al. |
| 2012/0225124 A1 | 9/2012 | Sadafi et al. |
| 2013/0028866 A1 | 1/2013 | Gilgun et al. |
| 2013/0029916 A1 | 1/2013 | Gilgun et al. |
| 2013/0035390 A1* | 2/2013 | Kloog et al. .................. 514/564 |
| 2013/0096158 A1 | 4/2013 | Hallak et al. |
| 2013/0184310 A1 | 7/2013 | Haviv et al. |
| 2013/0203807 A1 | 8/2013 | Tarcic et al. |
| 2013/0217724 A1 | 8/2013 | Ioffe et al. |
| 2013/0259856 A1 | 10/2013 | Kaye |
| 2013/0272996 A1 | 10/2013 | Tarcic et al. |
| 2013/0303569 A1 | 11/2013 | Bar-Zohar et al. |
| 2013/0345256 A1 | 12/2013 | Laxer et al. |
| 2013/0345257 A1 | 12/2013 | Hahn et al. |
| 2014/0017226 A1 | 1/2014 | Kaye et al. |
| 2014/0018386 A1 | 1/2014 | Sarfati et al. |
| 2014/0024678 A1 | 1/2014 | Sadafi et al. |
| 2014/0045886 A1 | 2/2014 | Martino et al. |
| 2014/0045887 A1 | 2/2014 | Martino et al. |

FOREIGN PATENT DOCUMENTS

| | | | |
|---|---|---|---|
| EP | 1095021 | 5/2001 | |
| EP | 1097139 | 5/2001 | |
| EP | 1511732 | 3/2005 | |
| EP | 1720531 | 11/2006 | |
| WO | WO 90/15052 | 12/1990 | |
| WO | WO 96/07601 | 3/1996 | |
| WO | WO 99/55678 | 11/1999 | |
| WO | WO 00/03991 | 1/2000 | |
| WO | WO 00/03992 | 1/2000 | |
| WO | WO 00/74654 | 12/2000 | |
| WO | WO 01/30758 | 5/2001 | |
| WO | WO 0130758 A1 * | 5/2001 | ........... C07D 215/54 |
| WO | WO 02/018343 | 3/2002 | |
| WO | WO 2003/106424 | 12/2003 | |
| WO | WO 2004/013153 | 2/2004 | |
| WO | WO 2005/041940 | 5/2005 | |
| WO | WO 2005/074899 | 8/2005 | |
| WO | WO 2012/069202 | 5/2012 | |
| WO | WO 2012/175541 | 12/2012 | |
| WO | WO 2013/169746 | 11/2013 | |

OTHER PUBLICATIONS

PCT International Preliminary Report On Patentability issued Apr. 23, 2008 in connection with PCT International Application No. PCT/US2006/040925.

PCT International Search Report issued Mar. 10, 2014 in connection with PCT International Application No. PCT/US13/67686.

Written Opinion of the International Searching Authority issued Mar. 10, 2014 in connection with PCT International Application No. PCT/US13/67686.

Brunmark et al. (2002) "The new orally active . . . effectively inhibits development and relapses of experimental autoimmune encephalomyelitis." J. of Neuroimmunology. 13:163-17.

Furniss, B et al. "Recrystallization Techniques", Vogel's Textbook of Practical Organic Chemistry, 5th ed., New York: John Wiley & Sons Inc. 1989.

Nelson, Drug Metabolism and Disposition, vol. 31, No. 12, pp. 1481-1498 (2003).

Thompson, Claire (2003) "Investigating the Fundamentals . . . Microscopy" Thesis submitted to the University of Nottingham for the Degree of Doctor of Philosophy, May 2003.

Tuvesson et al. (2005) "Cytochrime P450 3A4 is the Major enzyme Responsible . . . Laquinimod, a Novel Immunomodulator" Drug Metabolism and Disposition. 33(6):866-872.

Jansson, K. et al. (2006) "Synthesis and Reactivity of a Laquinimod, a Quinoline-3-carboxamide: Intramolecular transfer of the enol proton to a nitrogen atom as a plausible mechanism for ketene formation" J. Org. Chem. 71(4): 1658-1667.

* cited by examiner

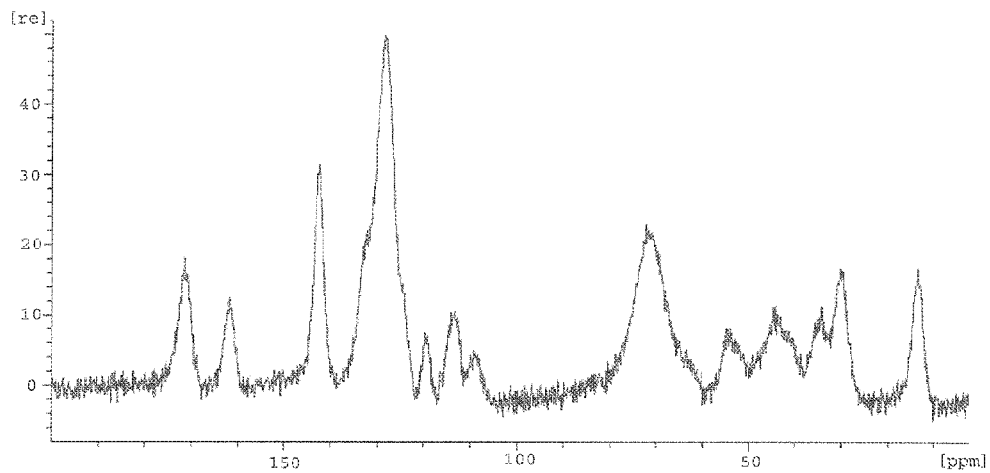
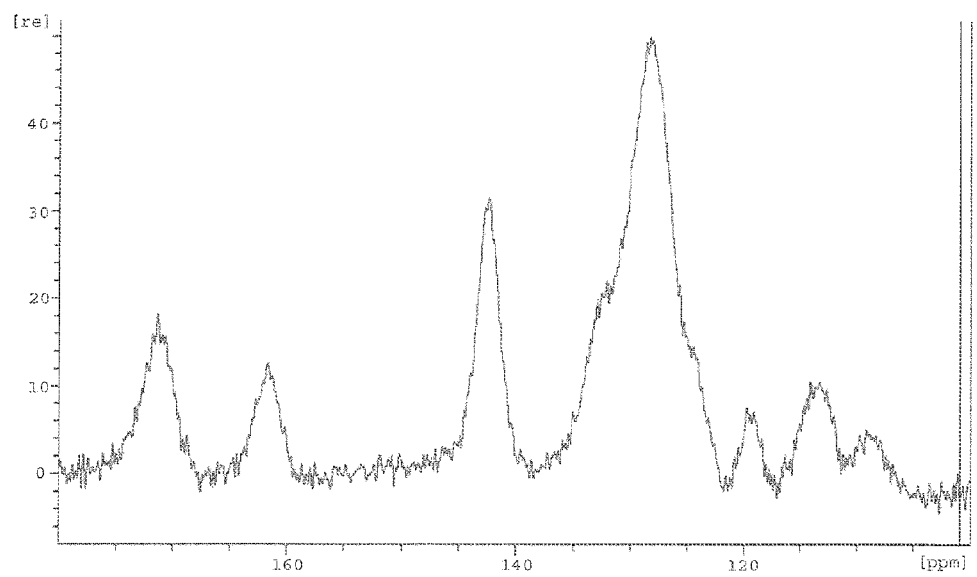

AMINE SALTS OF LAQUINIMOD

This application claims benefit of U.S. Provisional Application No. 61/723,495, filed Nov. 7, 2012, the entire content of which is hereby incorporated by reference herein.

Throughout this application, various publications, published patent applications, and patents are referenced. The disclosures of these documents in their entireties are hereby incorporated by reference into this application in order to more fully describe the state of the art to which this invention pertains.

BACKGROUND OF THE INVENTION

U.S. Pat. Nos. 7,989,473 and 8,178,127 disclose stable preparations of N-ethyl-N-phenyl-1,2-dihydro-4-hydroxy-5-chloro-1-methyl-2-oxoquinoline-3-carboxamide (CAS Number 248281-84-7), also known as laquinimod (laq.). Laquinimod has been shown in U.S. Pat. No. 6,077,851 to be effective in the acute experimental autoimmune encephalomyelitis (aEAE) model. U.S. Pat. No. 6,077,851 discloses the synthesis of laquinimod and the preparation of its sodium salt. U.S. Pat. No. 6,875,869 discloses an additional synthesis process of laquinimod.

PCT International Application Publication No. WO 2005/074899 discloses pharmaceutical compositions comprising laquinimod sodium.

U.S. Pat. No. 7,589,208 discloses the aqueous solubility of Li, Na, Ca, Cu, Zn, Fe and Mn salts of laquinimod and the experimental preparation of Na, Ca, Fe(III), Li and Zn salts of laquinimod.

SUMMARY OF THE INVENTION

The subject invention provides a Laquinimod amine salt, which is laquinimod meglumine, laquinimod choline hydroxide, laquinimod L-lysine or laquinimod monoethanolamine.

BRIEF DESCRIPTION OF THE FIGURES

FIG. 5A: Solid state $^{13}$C-NMR spectrum for amorphous Meglumine salt of Laquinimod in the 0-180 ppm range (batch 1) 1.3 ppm/161.1 Hz, Peaks: 171.6212, 161.5944, 142.4736, 128.2495, 119.3887, 113.5591, 109.3619, 72.0529, 54.3312, 44.3044, 34.5108, 29.8472, 13.5245.

FIG. 5B: Solid state $^{13}$C-NMR spectrum for amorphous Meglumine salt of Laquinimod in the 100-180 ppm range (batch 1), 100.93 ppm/12693.06 Hz, Peaks: 171.6212, 168.4172, 161.5944, 142.4736, 128.2495, 119.3887, 113.5591, 109.3619.

DETAILED DESCRIPTION OF THE INVENTION

The subject invention provides a Laquinimod amine salt, which is laquinimod meglumine, laquinimod choline hydroxide, laquinimod L-lysine or laquinimod monoethanolamine.

Figure 1:
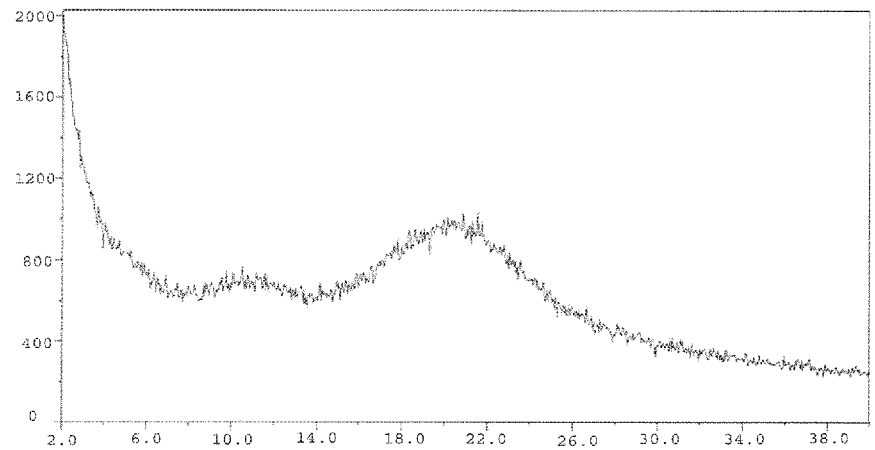
FIG. 1: XRD diffractogram for amorphous LAQ Meglumine salt of Laquinimod batch 1 with spin.
Figure 2:
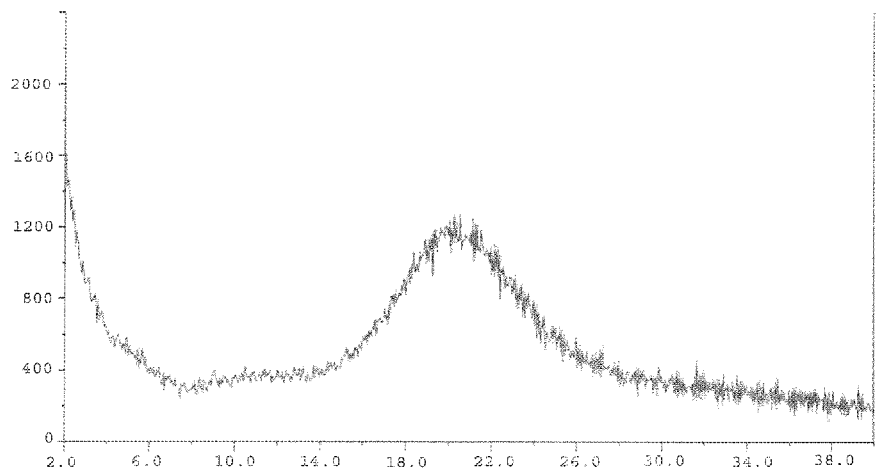
FIG. 2: XRD diffractogram for amorphous LAQ Meglumine salt of Laquinimod batch 3 with spin.
Figure 3:
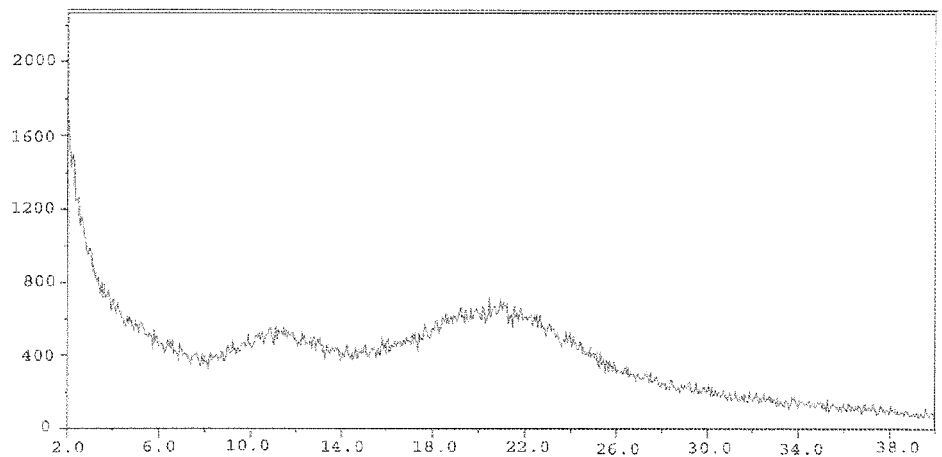
FIG. 3: XRD diffractogram for amorphous LAQ Meglumine salt of Laquinimod batch 4 with spin.
Figure 4A:
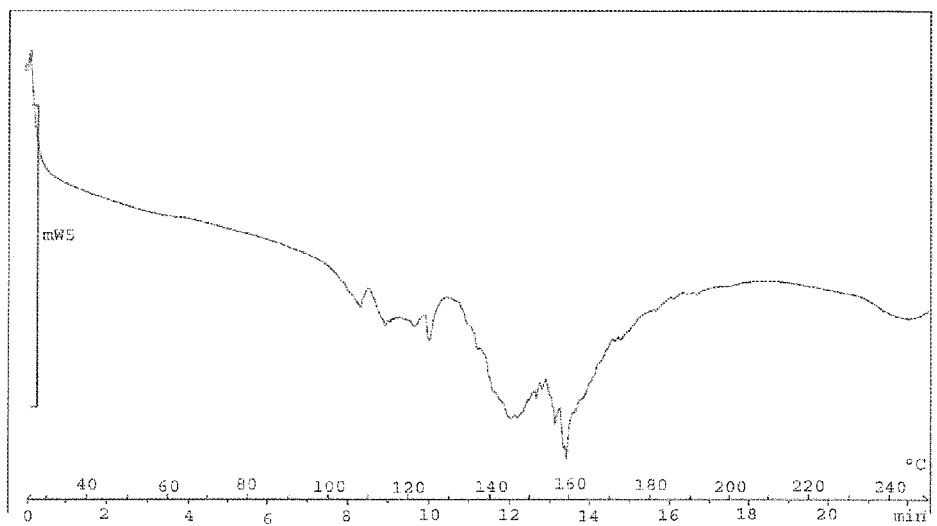
FIG. 4A: DSC thermogram scan of Meglumine salt of Laquinimod (batch 3), 4.2640 mg, Method: 25-250 C 10 C/min 40 ml/min N2 (QC-Tech-cr) 25.0-250.0° C. 100° C./min N2 40.0 ml/min.
Figure 4B:
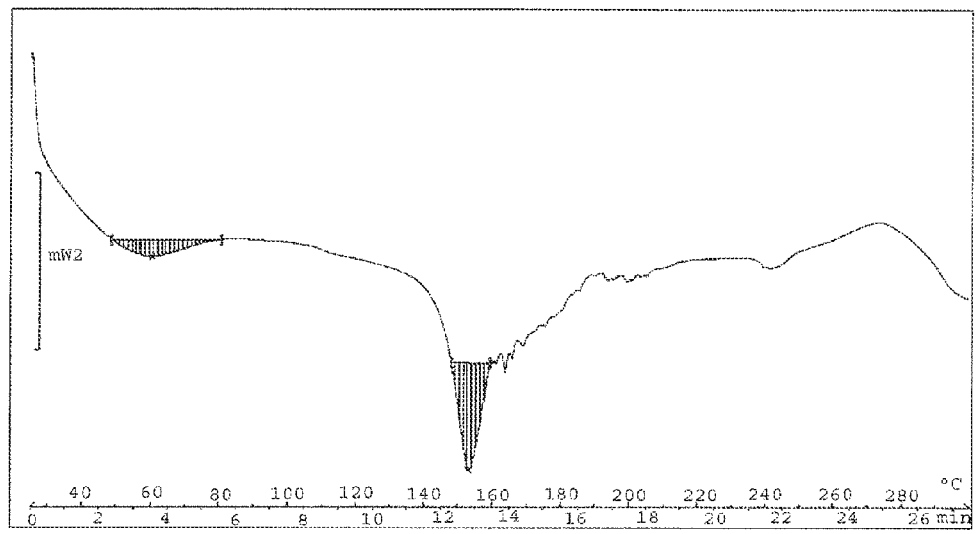
FIG. 4B: DSC thermogram scan of Meglumine salt of Laquinimod (batch 1), 2.6140 mg, Method: 25-300 C 10 C/min N2 (QC-Tech) 25.0-300.0° C. 100° C./min N2 40.0 ml/min, Peaks: (1) Integral −20.33 mJ Normalized −7.78 Jg$^{-1}$ Peak 60.46° C. Left limit 48.55° C. Right limit 80.96° C., (2) Integral −46.07 mJ Normalized −17.62 Jg$^{-1}$ Peak 152.84° C. Lef limit 147.84° C. Right limit 158.48° C.
Figure 4C:
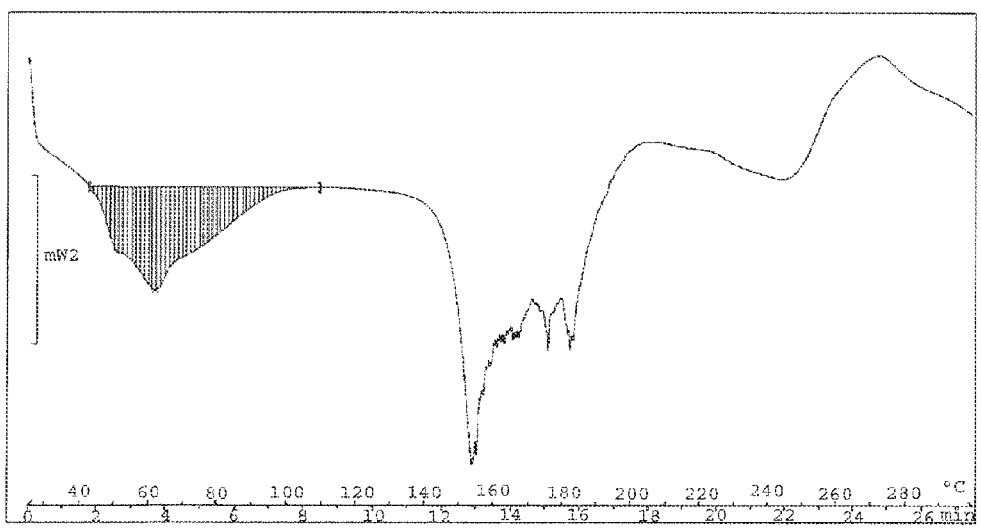
FIG. 4C: DSC thermogram scan of Meglumine salt of Laquinimod (batch 4), 4.1280 mg, Method: 25-300 C 10 C/min 40 ml/min N2 (QC-tech) 25.0-300.0° C. 10.00° C./min N2 40.0 ml/min, Peak: Integral −203.80 mJ Normalized −49.37 Jg$^{-1}$ Peak 61.95° C. Left limit 42.91° C. Right limit 109.95° C.

In one embodiment, the laquinimod amine salt is laquinimod meglumine. In another embodiment, the laquinimod meglumine is isolated. In another embodiment, the laquinimod meglumine is characterized by a DSC thermogram as shown in FIGS. 4A, B and C. In another embodiment the laquinimod meglumine is characterized by a solid-state $^{13}$C NMR spectrum with broad peak at 60-77, broad peak at 122-134, peak at 142.2 and 171.3±0.2 ppm. In yet another embodiment the laquinimod meglumine is characterized by a solid state $^{13}$C NMR as shown in FIGS. 5A and 5B.

Figure 6A:
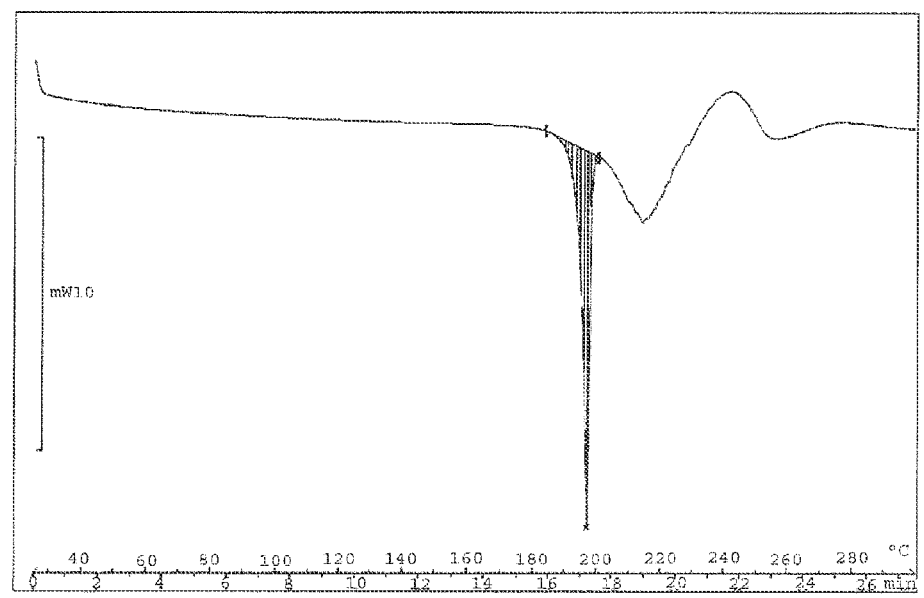
FIG. 6A: DSC thermogram scan of Choline salt of Laquinimod (batch 5), 3.1820 mg, Method: 25-300 C 10 C/min 40 ml/min N2 (QC-tech) 25.0-300.0° C. 10.00° C./min N2 40.0 ml/min, Peak: Integral −204.59 mJ Normalized −64.30 Jg$^{-1}$ Peak 196.50° C. Left limit 183.85° C. Right limit 201.00° C.
Figure 6B:
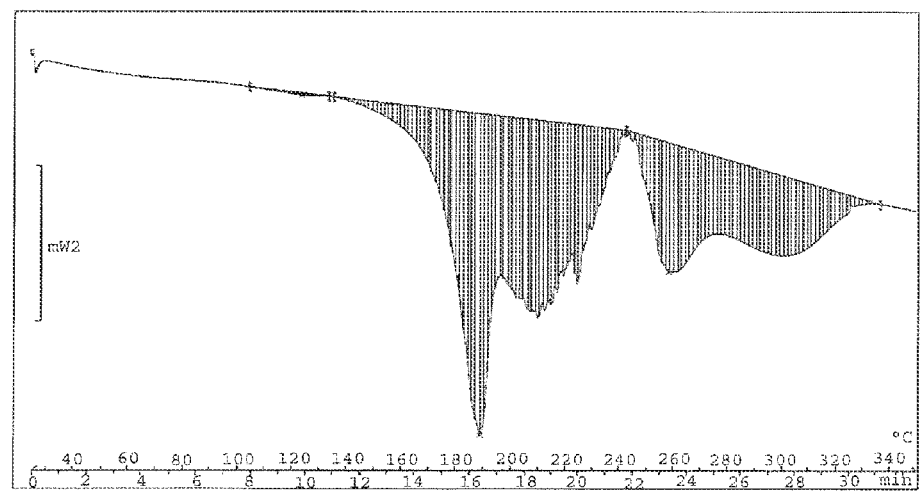
FIG. 6B: DSC thermogram scan of Choline salt of Laquinimod (batch 6), 3.4960 mg, Method: 25-350 C 10 C/min 40 ml/min N2 (QC-tech-cr) 25.0-350.0° C. 10.00° C./min N2 40.0 ml/min, Peaks: (1) Integral −2.36 mJ Normalized −0.67 Jg$^{-1}$ Peak 123.62° C. Left limit 103.92° C. Right limit 133.81° C., (2) Integral −885.25 mJ Normalized −253.22 Jg$^{-1}$ Peak 188.58° C. Left limit 134.97° C. Right limit 242.75° C., (3) Integral −468.82 mJ Normalized −134.10 Jg$^{-1}$ Peak 258.48° C. Left limit 242.77° C. Right limit 336.61° C.
Figure 6C:
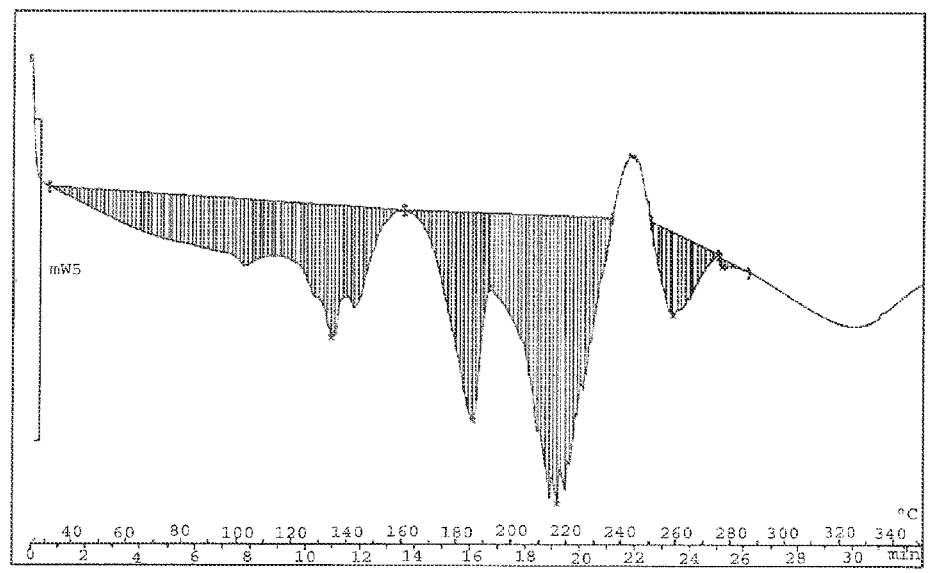
FIG. 6C: DSC thermogram scan of Choline salt of Laquinimod (batch 6), 6.0640 mg, Method: 25-350 C 10 C/min 40 ml/min N2 (QC-tech-cr) 25.0-350.0° C. 10.00° C./min N2 40.0 ml/min, Peaks: (1) Integral −584.87 mJ Normalized −96.45 Jg$^{-1}$ Peak 134.13° C. Left limit 31.32° C. Right limit 160.71° C., (2) Integral −253.79 mJ Normalized −41.85 Jg$^{-1}$ Peak 185.53° C. Left limit 160.88° C. Right limit 191.78° C., (3) Integral −644.96 mJ Normalized −106.36 Jg$^{-1}$ Peak 216.28° C. Left limit 191.78° C. Right limit 236.59° C., (4) Integral −105.19 mJ Normalized −17.35 Jg$^{-1}$ Peak 258.56° C. Left limit 250.07° C. Right limit 275.58° C., (5) Integral −2.85 mJ Normalized −0.47 Jg$^{-1}$ Peak 276.58° C. Left limit 275.76° C. Right limit 286.53° C.
Figure 6D:
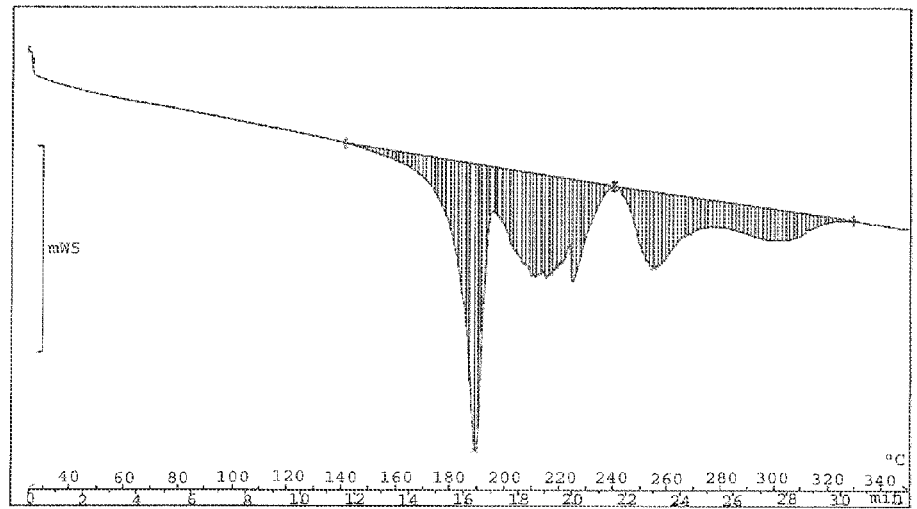
FIG. 6D: DSC thermogram scan of Choline salt of Laquinimod (batch 7), 3.7440 mg, Method: 25-350 C 10 C/min 40 ml/min N2 (QC-tech-cr) 25.0-350.0° C. 10.00° C./min N2 40.0 ml/min, Peaks: (1) Integral −868.62 mJ Normalized −232.00 Jg$^{-1}$ Peak 188.70° C. Left limit 140.72° C. Right limit 240.20° C., (2) Integral −381.62 mJ Normalized −101.93 Jg$^{-1}$ Peak 254.86° C. Left limit 240.49° C. Right limit 329.23° C.
Figure 6E:
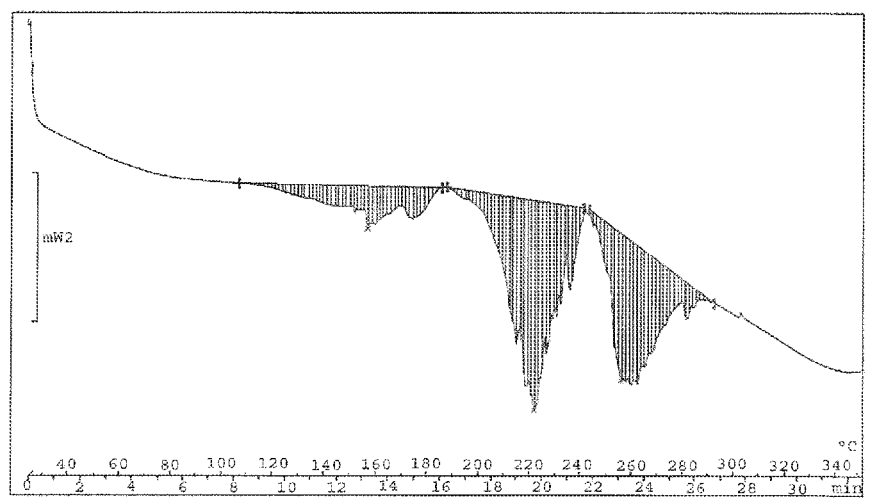
FIG. 6E: DSC thermogram scan of Choline salt of Laquinimod (batch 8), 4.0420 mg, Method: 25-350 C 10 C/min 40 ml/min N2 (QC-tech-cr) 25.0-350.0° C. 10.00° C./min N2 40.0 ml/min, Peaks: (1) Integral −104.57 mJ Normalized −25.87 Jg$^{-1}$ Peak 156.68° C. Left limit 106.47° C. Right limit 185.97° C., (2) Integral −333.47 mJ Normalized −82.50 Jg$^{-1}$ Peak 221.69° C. Left limit 167.42° C. Right limit 241.49° C., (3) Integral −244.65 mJ Normalized −80.53 Jg$^{-1}$ Peak 255.86° C. Left limit 243.32° C. Right limit 292.37° C.
Figure 7:
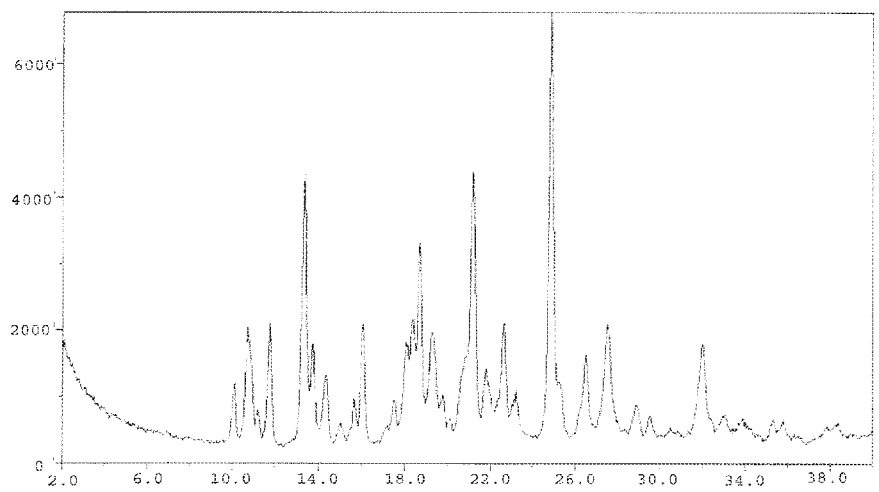
FIG. 7: XRD diffractogram for crystalline Laquinimod Choline salt of Laquinimod (batch 5 with spin), Temp 25.0° C., Step: 0.050° C., Integration Time 1.000 sec, Range: 2.000-40.000° Cont. Scan Rate: 3.000 [°/min] Vertical Scale Unit: [CPS] Horizontal Scale Unit [deg].
Figure 8:
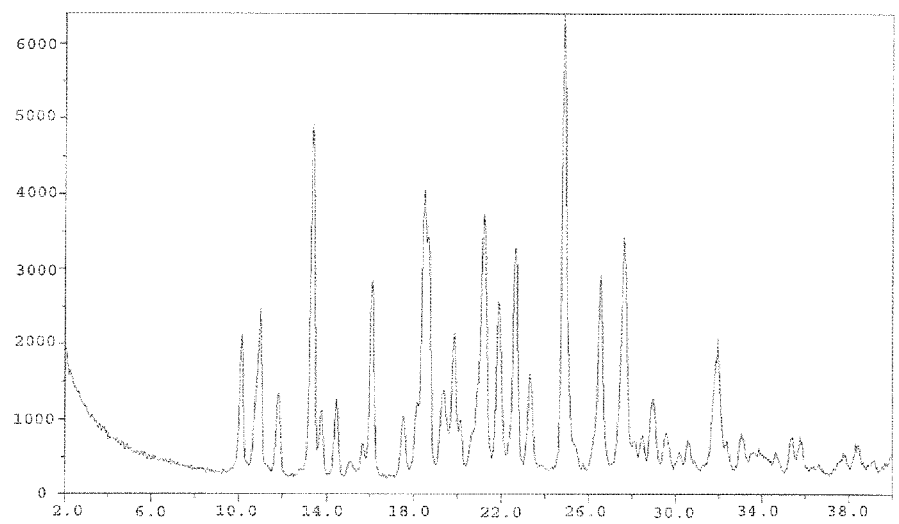
FIG. 8: XRD diffractogram for crystalline Laquinimod Choline salt of Laquinimod (batch 8 with spin), Temp 25.0° C., Step: 0.050° C., Integration Time 1.000 sec, Range: 2.000-40.000° Cont. Scan Rate: 3.000 [°/min] Vertical Scale Unit: [CPS] Horizontal Scale Unit [deg].
Figure 9A:
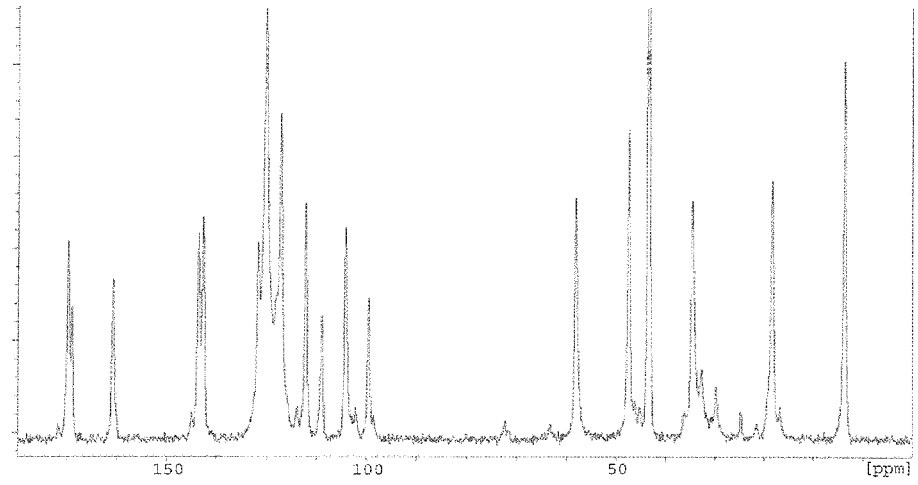
FIG. 9A: Solid state $^{13}$C-NMR spectrum for crystalline Choline salt of Laquinimod in the 0-180 ppm range (batch 5), Peaks: 169.7495, 168.9855, 160.7157, 143.6476, 142.6524, 131.6536, 130.1416, 127.9094, 127.1402, 122.1125, 118.8875, 114.1395, 109.5352, 68.0921, 57.4369, 53.6739, 44.5251, 28.2553, 13.7011.
Figure 9B:
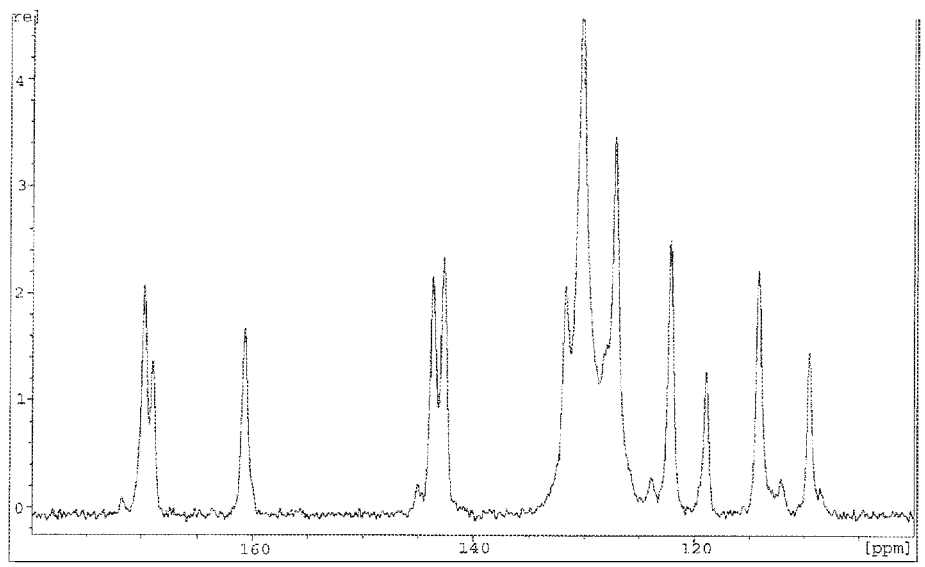
FIG. 9B: Solid state $^{13}$C-NMR spectrum for crystalline Choline salt of Laquinimod in the 100-180 ppm range (batch 5), Peaks: 169.7495, 168.9855, 160.7157, 143.6476, 142.6524, 131.6536, 130.1416, 127.9094, 127.1402, 122.1125, 118.8875, 114.1395, 109.5352.

In one embodiment, the laquinimod amine salt is laquinimod choline hydroxide. In another embodiment, the laquinimod choline hydroxide is isolated. In another embodiment, the laquinimod choline hydroxide is characterized by a DSC thermogram as shown in FIGS. 6A, B, C, D and E. In another embodiment, the laquinimod choline hydroxide is characterized by a powder XRD pattern with characteristic peaks at 10.1°, 11.8°, 13.4°, 14.4° and 16.1° 2-theta±0.2. In another embodiment, the laquinimod choline hydroxide is characterized by a powder XRD pattern with characteristic peaks at 19.3°, 21.2°, 22.7°, 24.8° and 27.6° 2-theta±0.2. In another embodiment, the laquinimod choline hydroxide is characterized by a powder XRD pattern as shown in FIGS. 7 and 8. In another embodiment, the laquinimod choline hydroxide is characterized by a solid-state $^{13}$C NMR spectrum with peaks at about 122.1, 127.2, 142.7 and 169.7±0.2 ppm. In another embodiment, the laquinimod choline hydroxide is characterized by a solid-state $^{13}$C NMR spectrum having chemical shifts differences between the signal exhibiting the lowest chemical shift and another in the chemical shift range of 100 to 180 ppm of about 12.6, 17.7, 33.2 60.2 and ±0.1 ppm. In another embodiment, the laquinimod choline hydroxide is characterized by a solid state $^{13}$C NMR as shown in FIGS. 9A and B. In another embodiment, the laquinimod choline hydroxide is in crystalline form. In yet another embodiment, the laquinimod choline hydroxide is in amorphous form.

Figure 10A:
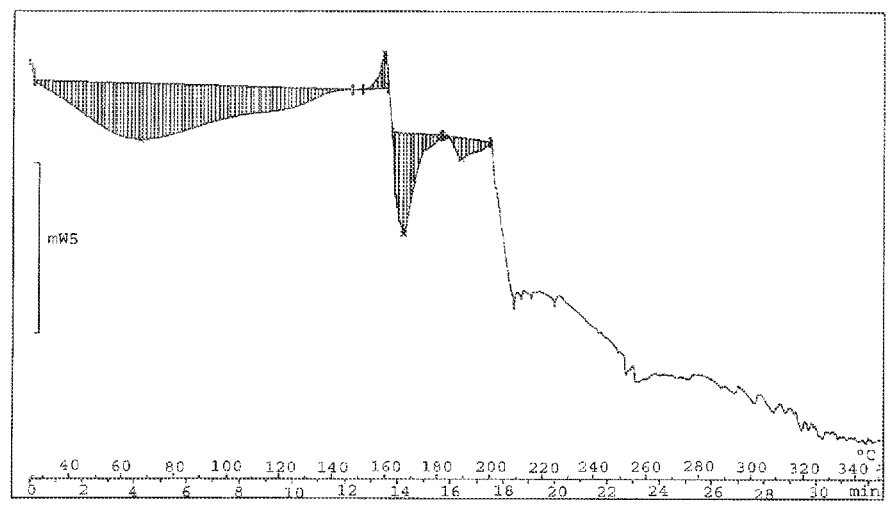
FIG. 10A: DSC thermogram scan of Lysine salt of Laquinimod (batch 9), 4.0560 mg, Method: 25-350 C 10 C/min 40 ml/min N2 (QC-tech-cr) 25.0-350.0° C. 10.00° C./min N2 40.0 ml/min, Peaks: (1) Integral −645.89 mJ Normalize −159.24 Jg$^{-1}$ Peak 66.74° C. Left limit 25.84° C. Right limit 147.72° C., (2) Integral 20.84 mJ Normalized 5.14 Jg$^{-1}$ Peak 159.80° C. Left limit 150.91° C. Right limit 161.08° C., (3) Integral −140.93 mJ Normalized −34.75 Jg$^{-1}$ Peak 166.74° C. Left limit 162.41° C. Right limit 161.57° C., (4) Integral −33.38 mJ Normalized −8.23 Jg$^{-1}$ Peak 188.68° C. Left limit 181.71° C. Right limit 200.00° C.
Figure 10B:
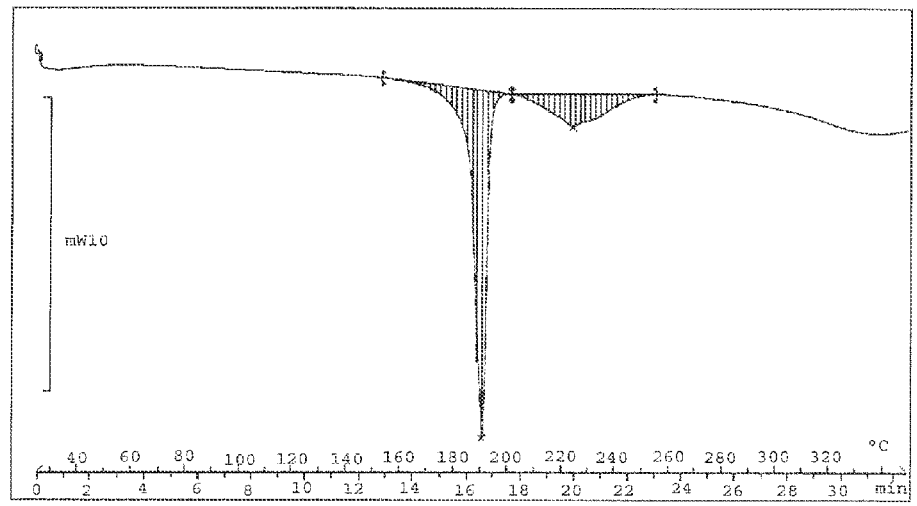
FIG. 10B: DSC thermogram scan of Lysine salt of Laquinimod (batch 10), 3.2900 mg, Method: 25-350 C 10 C/min 40 ml/min N2 (QC-tech-cr) 25.0-350.0° C. 10.00° C./min N2 40.0 ml/min, Peaks: (1) Integral −415.98 mJ Normalized −126.44 Jg$^{-1}$ Peak 190.02° C. Left limit 153.59° C. Right limit 201.57° C., (2) Integral −151.86 mJ Normalized −46.16 Jg$^{-1}$ Peak 224.32° C. Left limit 201.57° C. Right limit 255.37° C.
Figure 10C:
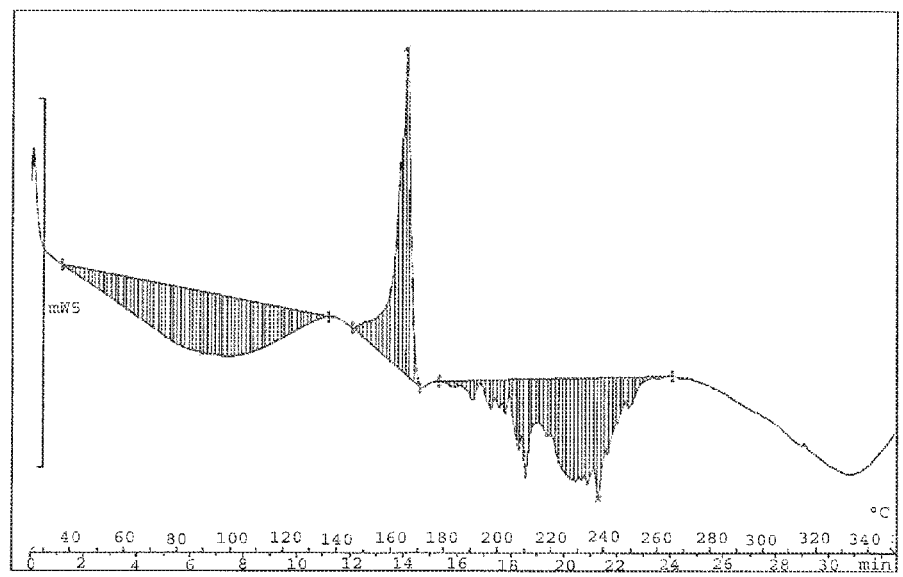
FIG. 10C: DSC thermogram scan of Lysine salt of Laquinimod (batch 11), 4.1600 mg, Method: 25-350 C 10 C/min 40 ml/min N2 (QC-tech-cr) 25.0-350.0° C. 10.00° C./min N2 40.0 ml/min, Peaks: (1) Integral −293.12 mJ Normalized −70.46 Jg$^{-1}$ Peak 89.26° C. Left limit 36.30° C. Right limit 136.98° C., (2) Integral 159.89 mJ Normalized 38.43 Jg$^{-1}$ Peak 166.08° C. Left limit 145.39° C. Right limit 171.19° C., (3) Integral −294.74 mJ Normalized −70.85 Jg$^{-1}$ Peak 237.62° C. Left limit 177.87° C. Right limit 265.80° C.
Figure 11:
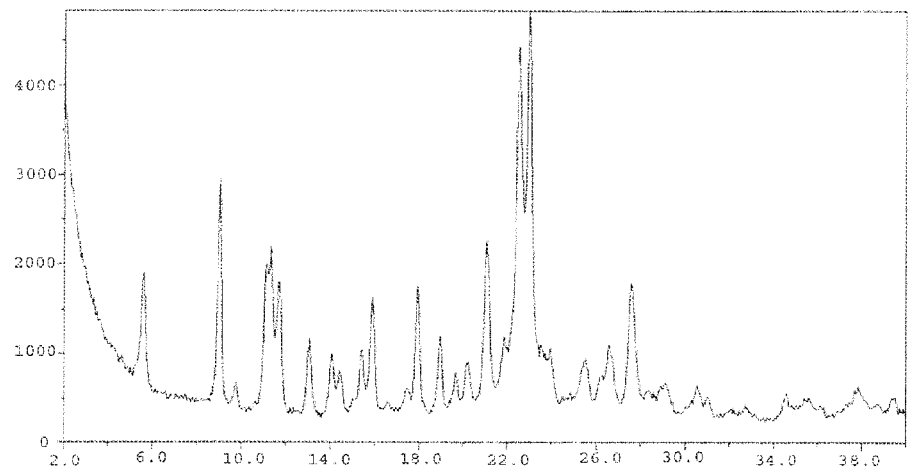
FIG. 11: XRD diffractogram for crystalline L-Lysine salt of Laquinimod (batch 10 with spin), Temp 25.0° C., Step: 0.050° C., Integration Time 1.000 sec, Range: 2.000-40.000° Cont. Scan Rate: 3.000 [°/min] Vertical Scale Unit: [CPS] Horizontal Scale Unit [deg].

In one embodiment, the laquinimod amine salt is laquinimod L-lysine. In another embodiment, the laquinimod L-lysine salt is isolated. In another embodiment, the laquinimod L-lysine is characterized the DSC thermogram as shown in FIGS. 10A, B and C. In another embodiment, the laquinimod L-lysine is characterized by a powder XRD pattern with characteristic peaks at 5.6°, 9.0°, 11.7°, 13.0° and 15.9° 2-theta±0.2. In another embodiment, the laquinimod L-lysine is characterized by a powder XRD pattern with characteristic peaks at 17.9°, 18.9°, 21.1°, 22.5° and 23.0° degrees 2-theta±0.2. In another embodiment, the laquinimod L-lysine is characterized by a powder XRD pattern as shown in FIG. 11. In another embodiment, the laquinimod L-lysine is in crystalline form. In yet another embodiment, the laquinimod L-lysine is in amorphous form.

Figure 12A:
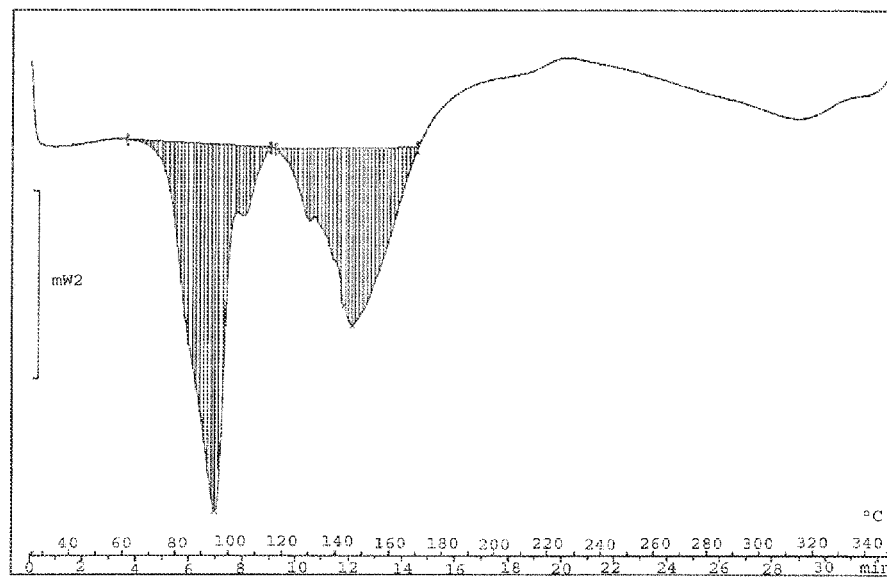
FIG. 12A: DSC thermogram scan of Monoethanolamine salt of Laquinimod (batch 14) 3.9820 mg, Method: 25-350 C 10 C/min 40 ml/min N2 (QC-tech-cr) 25.0-350.0° C. 10.00° C./min N2 40.0 ml/min, Peaks: (1) Integral −376.96 mJ Normalized −94.67 Jg$^{-1}$ Peak 94.34° C. Left limit 61.55° C. Right limit 115.82° C., (2) Integral −292.55 mJ Normalized −73.47 Jg$^{-1}$ Peak 146.21° C. Left limit 117.27° C. Right limit 170.96° C.
Figure 12B:
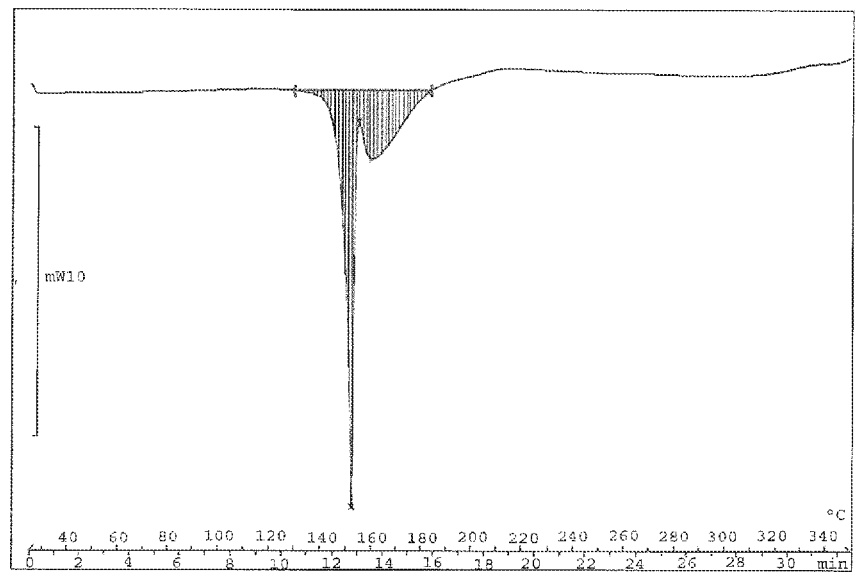
FIG. 12B: DSC thermogram scan of Monoethanolamine salt of Laquinimod (batch 15) 3.1960 mg, Method: 25-350 C 10 C/min 40 ml/min N2 (QC-tech-cr) 25.0-350.0° C. 10.00° C./min N2 40.0 ml/min, Peaks: (1) Integral −333.93 mJ Normalized −104.48 Jg$^{-1}$ Peak 151.94° C. Left limit 129.50° C. Right limit 155.29° C., (2) Integral −213.73 mJ Normalized −66.87 Jg$^{-1}$ Peak 160.40° C. Left limit 155.29° C. Right limit 184.07° C.
Figure 13:
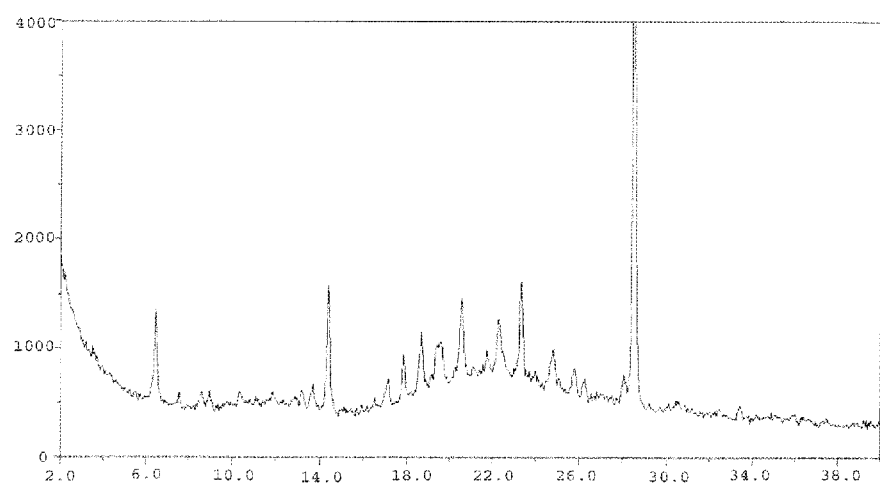
FIG. 13: XRD diffractogram for crystalline Monoethanolamine salt of Laquinimod (batch 4), Temp 25.0° C., Step: 0.050° C., Integration Time 1.000 sec, Range: 2.000-40.000° Cont. Scan Rate: 3.000 [°/min] Vertical Scale Unit: [CPS] Horizontal Scale Unit [deg]. The peak at 28.5 degrees two theta assign to addition of Silicon.
Figure 14:
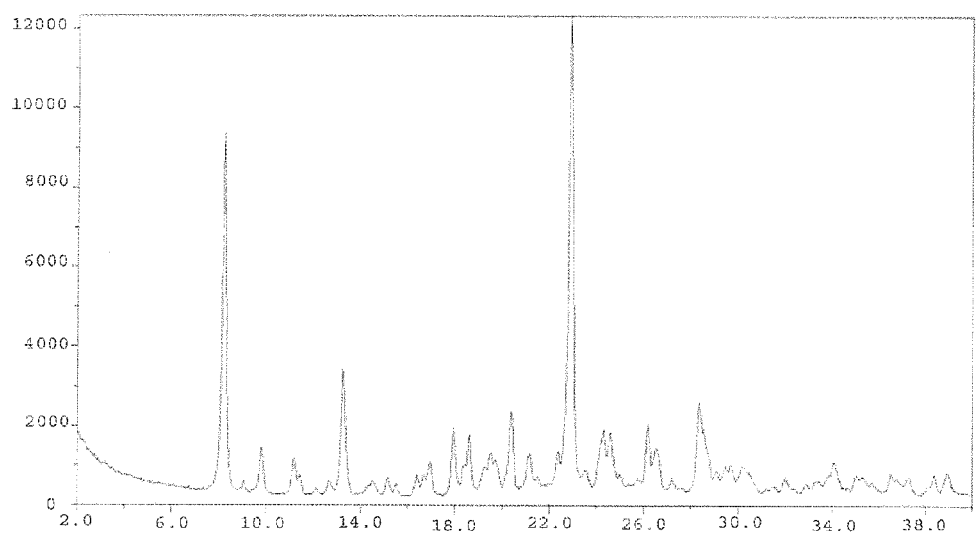
FIG. 14: XRD diffractogram for crystalline Monoethanolamine salt of Laquinimod (batch 5), Temp 25.0° C., Step: 0.050° C., Integration Time 1.000 sec, Range: 2.000-40.000° Cont. Scan Rate: 3.000 [°/min] Vertical Scale Unit: [CPS] Horizontal Scale Unit [deg]. The shoulder at 28.5 degrees two theta assign to addition of Silicon.

In one embodiment, the laquinimod amine salt is laquinimod monoethanolamine. In another embodiment, the laquinimod monoethanolamine is isolated. In another embodiment, the laquinimod monoethanolamine is characterized by a DSC thermogram as shown in FIG. 12A. In another embodiment, the laquinimod monoethanolamine is characterized by a powder XRD pattern with characteristic peaks at 6.5°, 14.4°, 17.9°, 18.7° and 20.6° 2-theta±0.2. In another embodiment, the laquinimod monoethanolamine is characterized by a powder XRD pattern with characteristic peaks at 17.1°, 19.4°, 22.3°, 23.3° and 24.8° degrees 2-theta±0.2. In another embodiment, the laquinimod monoethanolamine is characterized by a powder XRD pattern as shown in FIG. 13. In another embodiment, the laquinimod monoethanolamine is characterized by a DSC thermogram as shown in FIG. 12B. In another embodiment, the laquinimod monoethanolamine is characterized by a powder XRD pattern with characteristic peaks at 8.2°, 9.8°, 11.2°, 13.2° and 17.9° 2-theta±0.2. In another embodiment, the laquinimod monoethanolamine is characterized by a powder XRD pattern with characteristic peaks at 18.6°, 20.4°, 22.9°, 24.3° and 26.2° 2-theta±0.2. In another embodiment, the laquinimod monoethanolamine is characterized by a powder XRD pattern as shown in FIG. 14. In another embodiment, the laquinimod monoethanolamine is in crystalline form. In yet another embodiment, the laquinimod monoethanolamine is in amorphous form.

In one embodiment, the subject invention provides a pharmaceutical composition comprising a laquinimod amine salt and at least one pharmaceutical acceptable excipient. In another embodiment, the pharmaceutical composition further comprising laquinimod acid. In another embodiment, the pharmaceutical composition in which laquinimod acid is present in an amount of less than 1.5% based on the total laquinimod content of the pharmaceutical composition. In another embodiment, the pharmaceutical composition is free of laquinimod acid. In another embodiment, the pharmaceutical composition further comprising the sodium salt of laquinimod. In yet another embodiment, the pharmaceutical composition is free of the sodium salt of laquinimod.

In one embodiment, the subject invention provides a process for manufacture of laquinimod amine salt comprising: a) combining a solution of amine with laquinimod acid to form a first mixture; b) adding a solvent to the first mixture to form a second mixture; c) removing liquid from the second mixture; and d) recovering the laquinimod amine. In another embodiment, said amine is selected from the group consisting of meglumine, choline hydroxide, L-lysine and monoethanolamine. In yet another embodiment, the solvent added in step b) is selected from the group consisting of acetone, methanol, ethanol and dioxane or combination thereof, and in step c) the liquid is removed at ambient temperature and at reduced pressure.

In one embodiment, the subject invention provides a process for manufacture of the pharmaceutical composition comprising: a) obtaining laquinimod amine salt; and b) admixing the laquinimod amine salt with at least one pharmaceutical acceptable excipient.

In one embodiment, the subject invention provides a method for treating a subject afflicted with a form of multiple sclerosis or clinical isolated syndrome comprising administering to the subject a laquinimod amine salt pharmaceutical composition so as to thereby treat the subject.

In one embodiment, the subject invention provides a method for alleviating a symptom of multiple sclerosis in a subject afflicted with a form of multiple sclerosis comprising administering to the subject a laquinimod amine salt pharmaceutical composition so as to thereby alleviate the symptom of multiple sclerosis in the subject.

For the foregoing embodiments, each embodiment disclosed herein is contemplated as being applicable to each of the other disclosed embodiments.

Laquinimod can be administered in admixture with suitable pharmaceutical diluents, extenders, excipients, or carriers (collectively referred to herein as pharmaceutically acceptable carriers) suitably selected with respect to the intended form of administration and as consistent with conventional pharmaceutical practices. The unit will be in a form suitable for oral administration. Laquinimod can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar.

General techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

TERMS/DEFINITIONS

As used herein, unless stated otherwise, each of the following terms shall have the definition set forth below.

"About" in the context of a numerical value or range means±10% of the numerical value or range recited or claimed unless the standard error of the analytical measure used to obtain the numerical value results in a greater deviation.

A "salt" is salt of the instant compounds which have been modified by making acid or base salts of the compounds. The term "pharmaceutically acceptable salt" in this respect, refers to the relatively non-toxic, inorganic and organic acid or base addition salts of compounds of the present invention.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1, 0.2 . . . 0.9; and 1, 2, . . . 49 mg unit amounts are included as embodiments of this invention.

A characteristic of a compound refers to any quality that a compound exhibits, e.g., peaks or retention times, as determined by $^1H$ nuclear magnetic spectroscopy, $^{13}C$ nuclear magnetic spectroscopy, mass spectroscopy, infrared, ultraviolet or fluorescence spectrophotometry, gas chromatography, thin layer chromatography, high performance liquid chromatography (HPLC), elemental analysis, Ames test, dissolution, stability and any other quality that can be determined by an analytical method. Once the characteristics of a compound are known, the information can be used to, for example, screen or test for the presence of the compound in a sample. Quantity or weight percentage of a compound present in a sample can be determined by a suitable apparatus, for example, a HPLC.

As used herein, an "isolated" compound is a compound isolated from the crude reaction mixture following an affirmative act of isolation. The act of isolation necessarily involves separating the compound from the other known components of the crude reaction mixture, with some impurities, unknown side products and residual amounts of the other known components of the crude reaction mixture permitted to remain. Purification is an example of an affirmative act of isolation.

As used herein, a composition that is "free" of a chemical entity means that the composition contains, if at all, an amount of the chemical entity which cannot be avoided following an affirmative act intended to purify the composition by separating the chemical entity from the composition. A composition which is "free" of a laquinimod of a salt thereof, if present, as used herein, means that the laquinimod or a salt thereof is a minority component relative to the amount of 5-HLAQ, by weight.

As used herein, "stability testing" refers to tests conducted at specific time intervals and various environmental conditions (e.g., temperature and humidity) to see if and to what extent a drug product degrades over its designated shelf life time. The specific conditions and time of the tests are such that they accelerate the conditions the drug product is expected to encounter over its shelf life. For example, detailed requirements of stability testing for finished pharmaceuticals are codified in 21 C.F.R §211.166, the entire content of which is hereby incorporated by reference.

This invention relates to four amine salts of laquinimod which were surprisingly found to significantly increase solubility over known laquinimod salts and to be stable, and pharmaceutically processable. Solubility, specifically aqueous solubility, is a very important characteristic for pharmaceutical preparations, as solubility increases bioavailability. However, solubility alone is insufficient, as stability and pharmaceutical processability also impact the acceptability of a salt form of a drug. Often highly soluble salts are very hygroscopic and deliquescent under atmospheric air. Processing and storage of such deliquescent material is possible only in inert gas or by using dry rooms. The major problem with certain highly soluble materials is analysis. Fast water uptake by the salt can result in variable assay results. Thus certain highly hygroscopic forms are unacceptable.

Free laquinimod is a weak acid (pKa=4.2) and is almost insoluble in water, having an intrinsic solubility of about 0.007 mg/ml. Previously, sodium salt was the most soluble and stable known salt of laquinimod prepared, with an aqueous solubility of 138 mg/ml (U.S. Pat. No. 7,589,208).

Amine salts of certain active compounds have been shown to increase solubility, as compared to the corresponding sodium salt. However, there are many examples of compounds in the prior art for which meglumine, choline hydroxide, L-lysine and monoethanolamine salts did not substantially increase solubility.

Solubility
Meglumine

In certain contexts meglumine salt has increased solubility as compared to the corresponding sodium salt. Meglumine salt of ibuprofen increased solubility as compared to ibuprofen sodium salt, from 100 mg/ml (Sigma Aldrich Website) to 1290 mg/ml (U.S. Pat. No. 5,028,625).

However, there are many examples of when meglumine salt caused only a slight increase in solubility as compared to the corresponding sodium salt. U.S. Pat. No. 7,105,512 discloses a meglumine salt of meloxicam having an aqueous solubility of 2.3 mg/ml at pH 8.57, as compared to 2.0 mg/ml for the sodium salt at pH 8.06. U.S. Pat. No. 7,105,512 also discloses that, "the meglumine salt of meloxicam suffers from such problems that it has considerably low solubility in water and that if the amount thereof dissolved in water is increased, the pH value of the resulting solution abruptly increases to such an extent that the pH value is beyond the preferred range of from 5 to 9." (col. 2, lns. 18-23). Similar data was disclosed in U.S. Pat. No. 6,869,948. Triclosan meglumine salt solubility was 12.43 mg/ml, as compared to 5.95 mg/ml for the sodium salt (Grove, 2003). In comparison, the meglumine laquinimod salt solubility was 1050 or 1330 mg/ml, depending on preparation method and form (Table 6), as compared to 138 mg/ml for laquinimod sodium.

Meglumine salt has also in certain contexts increased solubility as compared to the corresponding free compound. The solubilities of meglumine salts of three amino nicotinic acid derivative compounds were 2.81, 0.478 and 0.210 mg/ml as compared to the corresponding free amino nicotinic acid derivative compounds, 0.004, 0.008 and 0.002 mg/ml respectively (PCT International Application Publication No. 2010/102826). Solubility of meglumine salt of ibuprofen was 1290 mg/ml as compared to free ibuprofen, 0.06 mg/ml (U.S. Pat. No. 5,028,625). However, these solubility increases are all at least an order of magnitude less than the solubility increase achieved by the meglumine salt of laquinimod which increased solubility from 0.007 mg/ml to 1050 or 1330 mg/ml, depending on preparation method and form (Table 6).

Choline Hydroxide

In certain contexts choline hydroxide salt has increased solubility as compared to the corresponding sodium salt. Choline salt of nimesulide provided high solubility and at the same time moderate solution alkalinity as compared to nimesulide sodium salt (European Patent Application No. 0869117A1).

However, there are many examples of when choline salt did not increase solubility or caused only a slight increase in solubility as compared to the corresponding sodium salt. U.S. Pat. No. 7,572,789 discloses a sodium salt of diazoxide with a solubility of 18.1 mg/ml at pH 7. Choline diazoxide salt solubility at the same pH was 41.5 mg/ml, only 2.3 times greater. Dicholine salt was found to have only twice the aqueous solubility of the disodium salt for the anti-cancer drug SNS-314 (Muller, 2009). U.S. Pat. No. 6,638,537 discloses choline salicylate salt as an insoluble compound. In comparison, the solubility of choline hydroxide salt of laquinimod was over 14 times greater than the sodium salt, 2000 or 2100 mg/ml depending on preparation and form, which is considered unlimited solubility (Table 6).

Choline salt has also in certain contexts increased solubility as compared to the corresponding free compound. The solubility of nimesulide choline was 500 mg/ml as compared to free nimesulide, 0.01 mg/ml (European Patent Application No. 0869117A1). The solubility of diclofenac choline was 250 mg/ml as compared to free diclofenac, 0.001 mg/ml. However, these solubility increases are all at least an order of magnitude less than the solubility increase achieved by the choline salt of laquinimod which increased solubility from 0.007 mg/ml to 2000 or 2100 mg/ml, depending on preparation method and form (Table 6).

L-Lysine

Regarding the L-lysine salt, there are many examples of when L-lysine salt did not increase solubility or caused only a slight increase in solubility as compared to the corresponding sodium salt. L-lysine salt does not offer significant increases in solubility for nimesulide or a CD80 antagonist (4-(6-Fluoro-3-oxo-1,3-dihydro-pyrazolo[4,3-c]cinnolin-2-yl)-N-(2,2-difluoroo-ethyl)-benzamide. L-lysine of nimesulide was found to be 7.5 mg/ml in water at pH 9.3 and 0.057 mg/ml at pH 6.8 (Piel, 1997). The solubility of the nimesulide-L-lysine salt represented only a slight improvement over nimesulide free acid form and no advantage over the corresponding sodium salt, which had a solubility of less than 10 mg/ml (European Patent Application No. 0869117A1). The L-lysine salt only provided a significant increase in solubility when used in a cyclodextrin complex. The L-lysine salt of the CD80 antagonist disclosed in PCT International Application Publication No. WO 2007/096588 offered no increase in solubility as compared to the sodium salt. In comparison, L-lysine laquinimod salt solubility was 1000 or 1176 mg/ml depending on preparation and form (Table 6), as compared to 138 mg/ml for laquinimod sodium.

L-lysine salt in some contexts increased solubility as compared to the corresponding free compound. The aqueous solubility of the nimesulide L-lysine salt discussed above was 7.5 mg/ml as compared to free nimesulide, 0.01 mg/ml. The free solubility of the CD80 antagonist discussed above was <0.5 mg/ml as compared to the L-lysine salt, <5 mg/ml. However, these solubility increases are all at least two orders of magnitude less than the solubility increase achieved by the L-lysine salt of laquinimod which increased solubility from 0.007 mg/ml to 1000 or 1176 mg/ml, depending on preparation method and form (Table 6).

Monoethanolamine

Regarding the monoethanolamine salt, there are many examples of when monoethanolamine salt did not increase solubility or caused only a slight increase in solubility as compared to the corresponding sodium salt. Monoethanolamine salt of triclosan was found to have an aqueous solubility of 5.84 mg/ml. Triclosan sodium benzoate salt solubility was 5.95 mg/ml, only slightly higher than the monoethanolamine salt (Grove 2003). U.S. Pat. No. 4,948,805 disclosed diclofenac monoethanolamine salt as being "practically insoluble." Sodium salt of Diclofenac was found to have a solubility of 13.6 mg/ml (pH 7.6). In comparison, Laquinimod monoethanoloamine salt solubility was 625 or 1176 mg/ml depending on method of preparation and form (Table 6), as compared to 138 mg/ml for laquinimod sodium.

Monoethanolamine salt in some contexts increased solubility as compared to the corresponding free compound. The solubility of the monoethanolamine salt of piroxicam was 126.2 mg/ml at pH 7.4 as compared to free piroxicam, 0.17 at pH 7.4 (Cheong, 2002). Solubility of meloxicam monoethanolamine was 8.36 mg/ml at pH 7.4 as compared to free meloxicam, 0.74 mg/ml at pH 7.4 (Ki, 2007). However, these solubility increases are at least an order of magnitude less than the solubility increase achieved by the monoethanolamine salt of laquinimod which increased solubility from 0.007 mg/ml to 625 or 1176 mg/ml, depending on preparation method and form (Table 6).

Stability and Form

It is important for pharmaceutical salts to be capable of being prepared in a manner that results in a physically stable form. However, the properties of salts are unpredictable with respect to both qualitative effect and to magnitude. European Patent Application No. 0869117A1 discloses that the choline salt of nimesulide is a highly crystalline solid with a melting point of 133-135° C., but that choline salts of the amino nicotinic acid derivative appeared as an oil or an amorphous solid. At the same time, meglumine salt of the amino nicotinic acid derivative compound is crystalline (PCT International Application Publication No. 2010/102826).

Additionally, solubility and hygroscopicity are generally inversely related to the stability of a salt. Low stability of certain hygroscopic solids is related to the presence of water. The absorbed water can form a layer of saturated solution above the surface of the solid particles. If susceptible, the material dissolved in the solution is exposed to liquid-phase degradation reactions and hydrolysis and oxidation that usually do not occur in sold phase (so called solvent-mediated reactions). Therefore isolation, processing and storage of highly soluble salts is generally problematic. The amine salts of laquinimod described herein, however, have very high aqueous solubility but demonstrate good physical stability when in contact with atmospheric air. Crystallinity is also important to stability, as an increase in amorphous nature can lead to increased hygroscopicity and thus a possible decrease in stability (Chen, 2009).

Tables 7A, 7B, 7C and 7D present the stability data for meglumine, choline hydroxide, L-lysine and monoethanolamine salts, respectively. All salts prepared in the experiments described herein demonstrate good physical stability under test conditions (refrigerator, atmospheric air). At the same time, preparation method was observed to affect solid stability for 3 of 4 salts prepared in this study. This is another example of the unpredictability of salt properties. Furthermore, the meglumine salt was only be synthesized in amorphous form, which would be expected to cause stability problems. However, two out of three samples of the laquinimod meglumine salt unexpectedly showed no physical change after 10 months of storage. The important conclusion is that all four salts could be prepared in processable and stable forms.

All four amine salts of laquinimod have extremely good aqueous solubility that is much higher than the sodium salt of laquinimod. The magnitude of these increases was unexpected as compared to the more modest and unpredictable changes in solubility found for corresponding salts in the prior art. All four salts can be prepared in a manner that results in physically stable laquinimod salts. Choline hydroxide, L-lysine and monoethanolamine can be synthesized in both crystalline and amorphous forms. Meglumine was only be synthesized as an amorphous solid yet unexpectedly did not have stability issues. This unpredictable balance of properties is a significant advantage of these Laquinimod amine salts.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

These examples describe the preparation and characterization of four novel laquinimod amine salts.

Four pharmaceutically acceptable amine bases with pKa >9 were used. Properties of the bases are summarized in Table 1.

TABLE 1

Properties of the amine bases

| Base | pKa | MW | Physical properties |
|---|---|---|---|
| Meglumine | 9.5 | 195.2 | Crystalline solid |
| Choline hydroxide | 13.9 | 104.17 | 46% aqueous solution |
| L-Lysisne | 8.95; 10.53 | 146.19 | Crystalline solid |
| Monoethanolamine | 9.50 | 61.08 | Volatile liquid |

List of Equipment:

X-Ray Diffraction (XRD)

Analysis was performed on ARL (SCINTAG) powder X-Ray diffractometer model X'TRA equipped with a solid state detector. Copper radiation of 1.5418 Å was used. Scanning parameters: range: 2-40 degrees two-theta; scan mode: continuous scan; step size: 0.05°, and a rate of 3 deg/min.

Solid state Carbon-13 Nuclear Magnetic Resonance Spectroscopy ($^{13}$C-NMR) The CP/MAS $^{13}$C NMR measurements were made on a Bruker Avance 500 NMR US/WB spectrometer in 4-mm ZrO$_2$ rotor. Magic angle spinning (MAS) speed was 10 kHz. As used herein, the term "$^{13}$C NMR chemical shifts" refers to the shifts measured under above specified conditions. These shifts can slightly differ from instrument to instrument and can be shifted either upfield or downfield due to the different instrumental setup and calibration used. Nevertheless, the sequence of individual peaks remains identical.

The Microscope used for morphology was a Nikon Eclipse, ME-600 equipped with a DeltaPix camera.

Example 1

Laquinimod Meglumine Salt

Meglumine, United States Pharmacopeial Convention (USP)/European Pharmacopeia (Ph.Eur) grade, manufactured by Merck and Co. Inc, was used in the experiments described herein. The preparation methods are summarized in Table 2 below and the chemical structure of the salt is presented below.

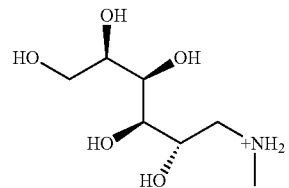

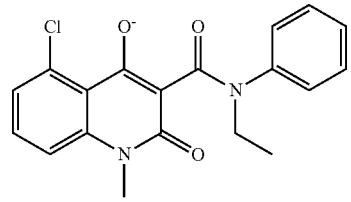

Reaction products appeared as solids and were subjected to analysis and characterized.

TABLE 2

Preparation of Meglumine salts of Laquinimod

Preparation method

| Exp. | Solvent (ratio) | LAQ:Meg (Moles) | Conditions | Product appearance |
|---|---|---|---|---|
| 1.1 | Acetone:water (30:2) | 1:1.05 | 20° C., antisolvent addition | Semi-solid |
|  | Acetone:water (30:2) | 1:1.05 | 45° C., vacuum evaporation | White solid |
| 1.2 | Acetone:methanol (40:15) | 1:1.01 | 20-5° C., antisolvent addition | No precipitation |
|  | Acetone:methanol (6.5:2) | 1:1.01 | 20° C. antisolvent addition | Semi-solid |
|  | Acetone:methanol (25:2) | 1:1.01 | 7-8° addition to antisolvent | Semi-solid |
| 1.3 | Dioxane:ethanol (31:3.5) | 1:1.01 | 6-12° addition to antisolvent | No precipitation |
|  | Dioxane:ethanol (31:3.5) | 1:1.01 | 20° vacuum evaporation | Semi-solid |
|  | Dioxane:ethanol (31:3.5) | 1:1.01 | 60° vacuum evaporation | White solid |
| 1.4 | Water | 1:1.01 | Lyophilization | White solid |

1.1. Precipitate Meglumine Salt from Solution: Batch 1

0.77 g of meglumine was dissolved in 10 ml water. 1.38 g of laquinimod acid was added by portions while stirring. The resulting mixture was heated to 50° C., and then 4 ml of water and 0.02 g of meglumine were added. The resulting solution (cloudy, pH=9-10) was cooled to +5° C. and held at this temperature for 36 hrs. No precipitation was observed.

The solution was evaporated under vacuum in a rotary evaporator (bath T=30-45° C.). The residue (3.51 g of colorless liquid) was stirred with magnetic stirrer and dry acetone was added by portions at ambient temperature.

After addition of 15 ml acetone, intensive precipitation was observed. The total volume of acetone introduced was 30 ml. The precipitate was a colorless, sticky honey-like material which was not filterable.

Isolation of Meglumine Salt by Evaporation:

The mixture was evaporated in a rotary evaporator under vacuum (bath T=45° C.). The residue, a white solid foam, was broken down with a spatula and dried at ambient temperature under high vacuum (2 mbar).

The solid product, 1.82 g of white powder, was sampled.

Analysis and Tests:

Solid State (SS) NMR confirmed salt formation. $^1$H and $^{13}$C NMR confirmed salt structure along with traces of acetone.

XRD identified amorphous structure.

Differential scanning calorimeter (DSC) identified amorphous structure.

Physical stability: A sample of powder was exposed to atmospheric air at relative humidity (RH)=38% in an open dish for 20 hours. No signs of aggregation or deliquescence were observed.

Samples of powder were stored in sealed transparent glass vials at +5° C. for 6 months. No physical change was observed. The samples were white flowable powder.

Aqueous solubility was 1330 mg/ml $H_2O$.

1.2. Salt Precipitation from Dry Solvent: (Batch 2)

0.77 g of meglumine was added to 20 ml of absolute methanol while stirring. The solution was then heated. Complete solid dissolution was observed at 37° C. and then 1.39 g of laquinimod acid was added and dissolved.

The resulting solution was cooled to 18° C. and 40 ml of dry acetone was added while stirring. Turbidity developed and the mixture was held in a refrigerator at +5° C. overnight.

A tiny amount of precipitate was formed.

The residue was evaporated under vacuum in a rotary evaporator (bath T=42° C.), the residue (3.52 g of colorless syrup) was stirred and 6.5 ml of dry acetone was added at ambient temperature.

Precipitation was observed. Precipitate was colorless, sticky, honey-like, and not filterable.

The mixture was evaporated under vacuum in a rotary evaporator (bath T=42° C.). The warm residue (3.77 g of colorless syrup) was introduced by drops into 25 ml of cold dry acetone at 7-8° C., on an ice-water bath.

Sticky semi-solid precipitate was formed.

1.3. Salt Precipitation by Solvent Exchange: (Batch 3)

The mixture from the previous experiment was heated to 40° C. and evaporated under vacuum in a rotary evaporator (bath T=42-60° C.), the residue (2.10 g of semi-solid product) was dissolved in 25 ml of absolute ethanol and evaporated under the same conditions.

The residue of the second evaporation (2.19 g of solid foam) was dissolved in 25 ml of absolute ethanol and evaporated under the same conditions.

The residue of the third evaporation (2.22 g) was dissolved in 3 ml of absolute ethanol, and the solution was added to cold 1,4-dioxane over a period of 45 minutes.

During the addition, the mixture was cooled on an ice-water bath and stirred vigorously.

No product precipitation was observed. Only a part of the dioxane was crystallized.

The mixture was evaporated under vacuum in a rotary evaporator at ambient temperature. After evaporation of half of the solvent, volume precipitation took place.

Sticky, semi-solid and not filterable precipitate (soft gum) formed.

Isolation of Salt by Evaporation:

Evaporation was continued while heating (bath T=60° C.). The residue, 2.16 g of solid white foam, was dried under high vacuum (2 mbar) at ambient temperature.

The dry product, 1.95 g of white powder was sampled.
Analysis and Tests:

XRD identified amorphous structure.

DSC identified amorphous structure and endotherm (endo) peaks at 48-80° C. and 147-162° C.

Physical stability: Samples of powder were stored in sealed transparent glass vials at +5° C. for 6 months. Physical change was observed. The sample was lumped white powder, with signs of deliquescence.

1.4. Isolation of Salt by Lyophilization: (Batch 4)

0.77 g of meglumine was dissolved in 10 ml of water, 1.39 g of laquinimod acid was added by portions while stirring. After dissolution, the solution was transferred to a polypropylene (PP) bottle with 2 ml of rinse water.

The solution was frozen at −18° C. and lyophilized at 0.11 mbar (collector temperature −84° C.) over a period of 22 hours.

After lyophilization was completed, the fragile solid cake (2.16 g) was broken up with a spatula. The resulting white powder was sampled.
Analysis and Tests:

$^1$H and $^{13}$C NMR confirmed structure.

XRD identified amorphous structure.

DSC identified amorphous structure and endo peaks at 42-109° C. and 147-162° C.

Physical stability: Samples of the powder were stored in sealed transparent glass vials at +5° C. for 6 months. No physical change was observed. The sample was a white powder with no signs of deliquescence.

Aqueous solubility was 1050 mg/ml $H_2O$.

Example 2

Laquinimod Choline Salt

Choline hydroxide, 46% wt. aqueous solution, supplied by Sigma-Aldrich, was used in the experiments described herein.

The experiments are summarized in Table 3 below and the chemical structure is presented below.

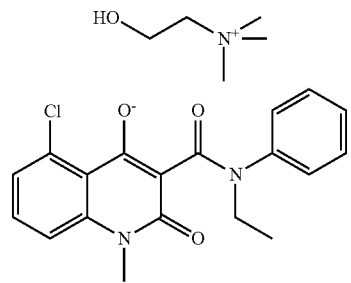

Reaction Products appeared as solids and were subjected to analysis and characterized.

TABLE 3

Preparation of Choline salts of Laquinimod

| | | Preparation method | | Product |
|---|---|---|---|---|
| Exp. | Solvent (ratio) | LAQ:Choline (Moles) | Conditions | appearance |
| 2.1 | Acetone | 1:1 | Precipitation from acetone at cooling | White powder |
| 2.2 | Water | 1:1 | Lyophilized from aqueous solution | White solid |
| 2.2.A | Water | 1:1 | Drying | Yellowish solid |
| 2.3 | Methanol:water (1.3:5) | 1:1 | Evaporation to dryness | White powder |

TABLE 3-continued

Preparation of Choline salts of Laquinimod

| Exp. | Preparation method | | | Product appearance |
|---|---|---|---|---|
| | Solvent (ratio) | LAQ:Choline (Moles) | Conditions | |
| 2.4 | 1,4 Dioxane:methanol (3:50) | 1:1 | Precipitation from solution | White powder |

2.1. Salt Precipitation by Solvent Exchange: (Batch 5)

0.80 g of choline hydroxide, 46% wt., was dissolved in 2 ml of water. 1.08 g of Laquinimod acid was added by portions while stirring. 1 ml of water was (rinse) added and complete dissolution was achieved.

20 ml of acetone was added to the resulting solution at ambient temperature while stirring. No precipitation was observed. The solution was evaporated under vacuum in a rotary evaporator (bath T=30-70° C.) to dryness.

The residue (1.46 g of colorless glassy solid) was dissolved in 20 ml of dry acetone and stirred at ambient temperature. After 5 minutes slow precipitation was observed.

The mixture was held in a refrigerator overnight at +6° C. and then filtered.

Wet solid product was dried in a vacuum oven at 40° C. up to constant mass.

The dry product was 1.07 g of white powder with a yield of 73.5%.

Analysis and Tests:

$^1$H and $^{13}$C NMR confirmed structure. Acid to base was ratio 1:1, and no residual solvents were detected.

XRD identified crystalline structure.

DSC identified melting point at 195° C.

2.2. Salt Isolation by Lyophilization: (Batch 6)

2.39 g Choline hydroxide 46% was dissolved in 5 ml of water. 3.24 g of laquinimod acid was added by portions. The solution was stirred vigorously, at ambient temperature, until dissolution.

The yellowish clear solution was transferred to a PP bottle, was frozen at −18° C. and lyophilized at 0.10-0.12 mbar (collector temperature −84° C.) over a period of 45 hours.

After lyophilization was completed, the solid cake product (4.41 g) contained two fractions:

brittle glassy solid (fraction A)

honey-like semi-solid material (fraction B)

The fractions were sampled separately.

Fraction B was collected and then exposed to atmospheric air over the period of a week. Physical transformation was observed.

The wet fraction B material (1.79 g) was dried under vacuum at 50° C. to constant weight. The result was 1.72 g of dry product (fraction B).

Analysis and Tests:

Main Fraction A $^1$H and $^{13}$C NMR—confirmed structure.

XRD identified amorphous structure.

DSC identified amorphous structure and endo peaks at 42-109° C. and 147-162° C.

Physical stability: Samples of the powder were stored in sealed transparent glass vials at +5° C. for 6 months. Physical change was observed. The sample was a yellowish semi-solid with signs of deliquescence.

Dry Fraction B

Appearance was a yellowish solid.

XRD identified crystalline structure.

DSC identified melting and degradation point at 195° C.

2.3. Salt Isolation by Solvent Evaporation (Batch 7)

2.44 g of choline hydroxide 46% was dissolved in 5 ml of absolute methanol and then 3.24 g of laquinimod acid was added by portions while stirring over a 10 min period. After additional stirring and complete dissolution, the solution was evaporated to dryness in a rotary evaporator under vacuum, (bath T=50-70° C.)

During the evaporation, honey-like residuum foamed at bath T=60-70° C. The foam solidified under vacuum at room temperature.

The residue, 4.19 g of solid foam, was broken up with a spatula and dried overnight under high vacuum (2 mbar) at room temperature.

The dry product was 4.17 g of white glassy powder.

Analysis and Tests:

XRD identified amorphous structure.

DSC identified amorphous structure, and endo peaks and degradation at T>185° C.

Physical stability: Samples of the powder were stored in sealed transparent glass vials at +5° C. for 6 months. No physical change was observed. The sample was white powder with no signs of deliquescence.

Aqueous solubility was >2100 mg/ml $H_2O$ (unlimited solubility).

2.4 Salt Isolation by Precipitation from Dioxane-Methanol (Batch 8)

2.44 g of choline hydroxide 46% was dissolved in 5 ml of absolute methanol and then 3.24 g of laquinimod acid was added by portions while stirring over a period of 10 minutes. After additional stirring and complete dissolution the solution was evaporated to dryness in a rotary evaporator under vacuum, (bath T=50-70° C.)

During the evaporation, the honey-like residuum foamed at bath T=60-70° C. The foam solidified under vacuum at room temperature.

The residue was 4.18 g of solid foam that was broken up with spatula and dissolved in 3 ml of absolute methanol and 50 ml of 1, 4 dioxane while stirring over a period of 20 min. During the addition, precipitation occurred. The mixture was stirred for one additional hour and filtered using a Büchner filter. The solid cake was washed with dioxane and dried in a vacuum oven at 50° C.

Dry product was 3.31 g of white powder, with a yield of 76.3%.

Analysis and Tests:

XRD identified crystalline structure.

DSC identified crystalline structure and melting point at 189° C.

Physical stability: Samples of the powder were stored in sealed transparent glass vials at +5° C. for 6 months. No physical change was observed. The sample was white powder with no signs of deliquescence.

Aqueous solubility was 2000 mg/ml $H_2O$ (unlimited solubility).

Example 3

Laquinimod L-Lysine Salt

L-Lysine >98%, supplied by Sigma-Aldrich, was used in the experiments described herein. Materials that appeared as solids were subjected to analysis and characterized.

The experiments are summarized in Table 4 below and chemical structure is presented below.

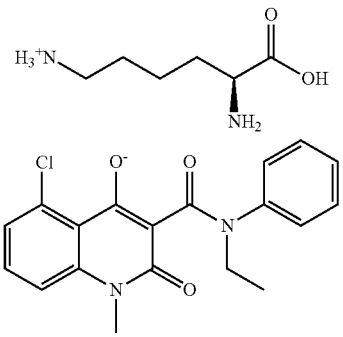

TABLE 4

Preparation of L-Lysine salts of Laquinimod

| Exp | Solvent (ratio) | LAQ:L-Lysine (Moles) | Conditions | Product appearance |
|---|---|---|---|---|
| 3.1 (1) | Water:acetone (6.3:50) | 1:1.02 | Precipitation from acetone-water | Liquid |
| 3.1 (2) | Acetone | 1:1.02 | Evaporation from acetone | White powder |
| 3.2 | Methanol:acetone (6:15) | 1:1 | Precipitation from methanol-water | White powder |
| 3.3 | Water | 1:1.03 | Evaporation from water | Off-white solid |

3.1 Isolation of Salt from Water-Acetone: (Batch 9)

1.0 g of L-Lysine was dissolved in 1.8 ml of water and 2.44 g of laquinimod acid was added to the solution while stirring. After partial dissolution, a very viscous gel-like solution was formed (pH=7).

An additional 4.5 ml of water and 0.02 g of L-Lysine were added while stirring, resulting in a clear solution (pH=8).

50 ml of acetone was added to the solution at ambient temperature while stirring continued. During the addition of acetone precipitation occurred.

The stirring was stopped and precipitate settled to the bottom. After 1 hour of settling, the precipitate formed a lower liquid layer.

The mixture was transferred to an evaporation flask with an additional 5 ml of water (rinse) and evaporated in a rotary evaporator under vacuum (bath T=45-50° C.). The residue, a colorless liquid, was dissolved in 25 ml of acetone and evaporation continued under the same conditions.

The residue, 3.48 g of white solid foam, was broken down with a spatula and dried at ambient temperature under high vacuum (2 mbar).

3.44 g of the white powder solid product was sampled.

Analysis and Tests:

$^1$H and $^{13}$C NMR confirmed structure and identified traces of acetone.

XRD identified amorphous structure.

DSC identified amorphous structure and degradation at T>140° C.

Physical stability: Samples of the powder were stored in sealed transparent glass vials at +5° C. for 6 months. No physical change was observed. The sample was white flowable powder.

Aqueous solubility was 1176 mg/ml $H_2O$ 3.2 Precipitation of Salt from Methanol-Acetone: (Batch 10)

1.0 g of L-Lysine was dissolved in 30 ml of absolute methanol and 2.44 g of laquinimod acid was added to the solution while stirring.

About two thirds of the resulting solution was evaporated in a rotary evaporator under vacuum. The residue, 7.9 g of solution, was stirred and 15 ml of dry acetone was added at ambient temperature. During the acetone addition solid precipitated. The mixture was stirred for an additional half hour and then introduced to a refrigerator (+5° C.) for 3 hours.

The solid product was collected by filtration, washed with 15 ml dry acetone and dried in an oven at 40° C. under vacuum.

Dry product was 3.19 g of white powder, with a yield of 92.7%

Analysis and Tests:

$^1$H and $^{13}$C NMR confirmed structure and identified traces of acetone.

XRD identified crystalline structure.

DSC identified crystalline structure and melting point at 190° C.

Physical stability: Samples of the powder were stored in sealed transparent glass vials at +5° C. for 6 months. No physical change was observed. The sample was white powder.

Aqueous solubility was 1000 mg/ml $H_2O$.

3.3 Salt Isolation by Solvent Evaporation: (Batch 11)

2.44 g of laquinimod acid was added to a solution of 1.0 g of L-Lysine in 10 ml of water at ambient temperature while stirring. After partial dissolution of the solid, an additional 0.03 g of L-Lysine was added (pH=7-8) and then the mixture was heated to 45° C.

The resulting solution was evaporated in a rotary evaporator under vacuum (bath T=65° C.)

During the evaporation, a syrup-like residuum foamed. The foam was solidified under vacuum.

The residue, 3.35 g of solid foam, was broken up with a spatula and dried overnight in an oven under vacuum at 40° C.

Dry product was 3.34 g of off-white solid.

Analysis and Tests:

$^1$H and $^{13}$C NMR confirmed structure.

XRD identified amorphous structure.

DSC identified amorphous structure and degradation at T>140° C.

Example 4

Laquinimod Ethanolamine Salt

Monoethanolamine (purity 99.7%), supplied by Sigma-Aldrich, was used in the experiments described herein. Materials that appeared as solids were subjected to analysis and characterized.

The experiments are summarized in Table 5 below and the chemical structure is presented below.

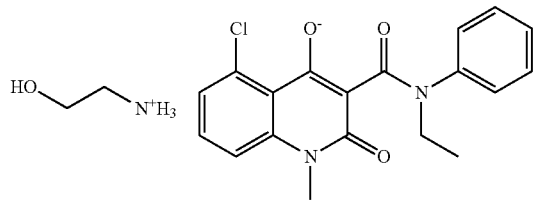

TABLE 5

Preparation of Ethanolamine salts of Laquinimod

Preparation method

| Exp | Solvent (ratio) | LAQ:EA (Moles) | Conditions | Product appearance |
|---|---|---|---|---|
| 4.1 | Acetone:water (50:6) | 1:1.02 | Evaporation from acetone-water | White powder |
| 4.2 | Water | 1:1.02 | Lyophilized from aqueous solution | White powder |
| 4.3 | 1,4 dioxane | 1:1.02 | Precipitation from dioxane | White powder |
| 4.4 | Acetone | 1:1.02 | Precipitation from acetone | White powder |

4.1 Salt Isolation by Solvent Evaporation: (Batch 12)

0.61 g of ethanolamine and 3.50 g of laquinimod acid were dissolved in 6 ml of water followed by 50 ml of acetone. No precipitation was observed.

The mixture was evaporated to dryness under vacuum in a rotary evaporator.

During the evaporation a residuum foamed. The foam was solidified under vacuum.

The residue, a solid glassy foam, was broken up with a spatula and dried overnight in oven under vacuum at 40° C.

Dry product was 2.62 g of white powder.

Analysis and Tests:

$^1$H and $^{13}$C NMR—confirmed structure and identified traces of acetone

XRD identified amorphous structure.

DSC identified amorphous structure, endo peaks at 40-100° C., and decomposition at 140-170° C.

Physical stability:

At room temperature:

A sample of white flowable powder was exposed to atmospheric air in air-conditioned room at RH=25-30%, T=18-20° C.

After 4 hours there was no change.

After 24 hours there was yellowish aggregated powder.

In refrigerator:

A sample of white flowable powder was stored in sealed transparent glass vials at +5° C. for 3 months. Physical change was observed. The sample was a yellowish aggregated powder.

4.2 Salt Isolation by Lyophilization: (Batch 13)

0.61 g of ethanolamine and 3.50 g of laquinimod acid were dissolved in 10 ml of water while stirring at ambient temperature. The solution was transferred to a PP container and lyophilized at 0.014-0.010 mbar (collector temperature −79 to −81° C.) over a period of 72 hours.

The product, 3.94 g of solid white glassy cake, was broken up with a spatula and the white powder was sampled.

Analysis and Tests:

$^1$H and $^{13}$C NMR confirmed structure.

XRD identified amorphous structure.

DSC identified amorphous structure, endo at 40-100° C., and decomposition at 140-170° C.

Physical stability: Sample of the powder was stored in sealed transparent glass vials at +5° C. for 3 months. The sample was an off-white powder.

Aqueous solubility was 1176 mg/ml $H_2O$.

4.3 Precipitation of Salt from Dioxane: (Batch 14)

0.61 g of ethanolamine was dissolved in 25 ml of dry methanol, then 3.50 g of laquinimod acid was added and dissolved while stirring.

The solution was evaporated under vacuum in a rotary evaporator (bath T=65° C.) and the obtained residue (4.38 g of semi-solid material) was dissolved in 10 ml of warm 1,4 dioxane.

White solid precipitate was formed. An additional 15 ml of dioxane was introduced and the resulting slurry was stirred at ambient temperature for 2 hours.

Solid product was collected by filtration, washed with 5 ml of dioxane and dried under vacuum in an oven at 40° C.

Dry product was 5.01 g of white solid, ground to white flowable powder.

Analysis and Tests:

$^1$H and $^{13}$C NMR-Confirmed structure, and identified 1 mole of dioxane-solvate.

XRD identified crystalline structure and form I (solvate).

DSC identified crystalline structure, melting point at 80-90° C., and decomposition at T>120° C.

Physical stability:

At room temperature:

A sample of white flowable powder was exposed to atmospheric air in an air-conditioned room at RH=25-30%, T=18-20° C.

After 4 hours there was no change.

After 16 hours there was aggregated white powder.

In refrigerator:

A sample of white flowable powder was stored in sealed transparent glass vials at +5° C. for 3 months. No physical change was observed. The material appears to be white powder.

4.4 Precipitation of Salt from Acetone: (Batch 15)

0.61 g of ethanolamine was dissolved in 20 ml of dry methanol, and then 3.50 g of laquinimod acid was added and dissolved while stirring.

The solution was evaporated to dryness under vacuum in a rotary evaporator (bath T=55° C.)

The residue was dissolved in 30 ml of warm dry acetone and evaporated under the same conditions.

Then the residue (4.4 g of white glassy foam) was dissolved in 20 ml of warm dry acetone and stirred at ambient temperature for 1 hour. White solid precipitate was formed and the mixture was stored in a refrigerator at +5° C.

Solid product was collected by filtration and dried under vacuum in an oven at 40° C.

Dry product was 3.44 g of white powder with a yield of 83%.

Analysis and Tests:

$^1$H and $^{13}$C NMR—confirmed structure and identified traces of acetone.

XRD identified crystalline structure, form II.

DSC identified crystalline structure and melting point at 150° C.

Physical stability:

At room temperature:

A sample of white flowable powder was exposed to atmospheric air in an air-conditioned room at RH=29-32%, T=18-20° C.

After 4 hrs there was no change; remained white powder.

After 25 hrs there was no change; remained white powder.

In refrigerator

A sample of white flowable powder was stored in sealed transparent glass vials at +5° C. for 3 months. Small physical change was observed. The material appears to be an off-white powder.

Aqueous solubility—625 mg/ml $H_2O$.

Results

Formation of Salt

All four amines of the invention formed highly soluble solid salts with laquinimod acid in aqueous media and/or polar organic solvent (methanol).

The isolated compounds appeared as a white powder.

Crystallinity of Laquinimod Amine Salts

The meglumine salt of laquinimod prepared by the above-described methods appeared as an amorphous solid.

The choline, lysine and monoethanolamine salts of laquinimod, prepared by precipitation, were crystalline compounds. The choline, lysine and monoethanolamine salts of laquinimod prepared by lyophilization and solvent evaporation were solid amorphous materials.

An important parameter affecting the salt crystallization is the presence of water in the crystallizing mixture. Even at low water concentration the salts precipitate as oil or semi-solid materials.

Solubility of Laquinimod Amine Salts

The amine base salts of the invention have an enhanced aqueous solubility over the sodium salt (Table 6).

TABLE 6

Solubility of Laquinimod salts

| Experiment | Salt | Preparation method (form) | Aqueous solubility, mg/ml |
|---|---|---|---|
|  | Existing Na salt | Crystallization from ethanol/water | 138* |
| 1.1 | Meglumine | Evaporation (amorphous) | 1330 |
| 1.4 |  | Lyophilization (amorphous) | 1050 |
| 2.3 | Choline | Evaporation (amorphous) | >2100** |
| 2.4 |  | Precipitation (crystalline) | >2000** |
| 3.1 | L-Lysine | Evaporation (amorphous) | 1176 |
| 3.2 |  | Precipitation (crystalline) | 1000 |
| 4.2 | Ethanolamine | Lyophilization (amorphous) | 1176 |
| 4.4 |  | Precipitation (crystalline) | 625 |

*U.S. Pat. No. 7,589,208
**unlimited solubility

The amine salts of the invention were very soluble in water according to the USP. The existing Na salt is only freely soluble to soluble. Amorphous forms of lysine and ethanolamine salts were found more soluble than the crystalline analogs.

Physical Stability of Laquinimod Amine Salts

TABLE 7.A

Physical stability of meglumine salt in glass vials at +5° C., air atmosphere

| Time, month | Batch 1 | Batch 4 | Batch 3 |
|---|---|---|---|
|  | Sample appearance: | | |
| 0 | White flowable powder | White flowable powder | White flowable powder |
| 5 | — | White flowable powder | Lumped white powder |
| 6 | White flowable powder | — | — |
| 0 | White flowable powder | White flowable powder | Lumped white to off-white powder, signs of deliquiscence |

TABLE 7.B

Physical stability of Choline salt in glass vials at +5° C., air atmosphere

| Time, month | Batch 6 | Batch 7 | Batch 8 |
|---|---|---|---|
|  | Sample appearance: | | |
| 0 | White glassy solid | White powder | White powder |
| 5 | Yellowish semi-solid, deliquescence | White powder | White powder |
| 9 | Yellowish semi-solid, deliquescence | White powder | White powder |

TABLE 7.C

Physical stability of L-Lysine salt in glass vials at +5° C., air atmosphere

| Time, month | Batch 10 | Batch 9 |
|---|---|---|
|  | Sample appearance | |
| 0 | White flowable powder | White flowable powder |
| 5 | White flowable powder | White flowable powder |
| 9 | White flowable powder | White flowable powder |

TABLE 7.D

Physical stability of ethanolamine salt in glass vials at +5° C., air atmosphere

| Sample: Time, month | Batch 12 | Batch 13 | Batch 14 | Batch 15 |
|---|---|---|---|---|
| 0 | White flowable powder | White powder | White flowable powder | White powder |
| 3 | Slightly yellowish aggregated powder | White powder | White flowable powder | Off-white powder |
| 7 | Yellowish aggregated powder | White slightly aggregated powder | White flowable powder | Off-white powder |

Meglumine salt: Batches 1 and 4 appeared as white flowable powders with no sign of physical change after 10 months of storage. In batch 3 physical change was observed after 5 months.

Choline salt: Batches 7 and 8 appeared as white powders with no sign of physical change after 9 months of storage, batch 6, prepared by lyophilization, developed color and deliquescence occurred after 5 months.

L-Lysine salt: Batches 10 and 9 appeared as white flowable powders with no sign of physical change after 9 months of storage.

Ethanolamine salt: Batch 14 appeared as white flowable powder with no sign of physical change after 7 months of storage. In batches 13 and 15 some changes were observed. In batch 13 slight aggregation was developed after 7 month of storage. In batch 15 color change was developed after 3 month. Amorphous material prepared by evaporation (batch 12) was less stable. Stronger color development and aggregation were observed in this sample.

The presented data demonstrates that all four amine salts can be prepared as processable and stable powders.

Laquinimod Salts Morphology and Particle Size, Microscopic Observation

Meglumine Salt:

Batch 1 was amorphous material prepared by vacuum evaporation from an acetone:water solution to dryness. The sample was white flowable powder. Particles were highly aggregated and irregular in size (300-1000 µm).

Batch 4 was amorphous material prepared by lyophilization from an aqueous solution. Sample was white flowable powder. Particles were aggregated and irregular. Most of the primary particles were 50-200 µm; aggregates were 500-2000 µm.

Choline Salt:

Batch 7 was amorphous material prepared by evaporation to dryness from a methanol solution. The sample was white powder. Particles were irregular, 200-2000 µm in size.

Batch 8 was crystalline material prepared by precipitation from dioxane:methanol. The sample was white powder. Particles were aggregated rod-shaped crystals, 2-10 µm in size.

L-Lysine Salt:

Batch 9 was amorphous material prepared by evaporation to dryness from an acetone-water solution. The sample was white flowable powder. Particles were irregular, 20-1000 µm in size.

Batch 10 was crystalline material prepared by precipitation from methanol-acetone. The sample was white flowable powder. Particles were highly aggregated rod-shape crystals, 5-10 µm in size.

Ethanolamine Salt:

Batch 12 was amorphous material prepared by evaporation to dryness, from a water-acetone solution. The sample was white flowable powder. Particles were irregular, 500-3000 µm in size.

Batch 13 was amorphous material prepared by lyophilization of an aqueous solution. Sample was white powder. Particles were irregular, 20-2000 µm in size.

Batch 14 was crystalline material (solvate with dioxane, Form I), prepared by precipitation from dioxane. The sample was white flowable powder. Particles were aggregated rod-shaped crystals, 20-80 µm in size.

Batch 15 was crystalline material (Form II) prepared by precipitation from acetone. The sample was white flowable powder. Particles were aggregated, irregular, rod and prism shaped crystals, 2-1010 µm in size.

REFERENCES

1. Chen, D. (2009) "Hygroscopicity of Pharmaceutical Crystals", *A Dissertation Submitted to the Faculty of the Graduate School of the University of Minnesota*. 19-22, retrieved Nov. 5, 2012, <conservancy.umn.edu/bitstream/47878/1/Chen_umn_0130E_10181.pdf>
2. Cheong, H.-A., Choi, H.-K. (2002) "Enhanced Percutaneous Absoption of Piroxicam via Salt Formation with Ethanolamines", *Pharm. Res.* 19:1357-1380.
3. European Patent Application No. 0869117A1, published Oct. 7, 1998.
4. Grove, C. et al. (2003) "Improving the aqueous solubility of triclosan by solubilization, complexation and in situ salt formation", *J. Cosmet. Sci.* 54:537-550.
5. Ki, H.-M., Choi H.-K. (2007) "The effect of meloxicam/ethanolamine salt formation on percutaneous absorption of meloxicam", *Arch. Pharm. Res.* 30(2):215-221.
6. Muller, C. (2009) "Prodrug Approaches for Enhancing the Bioavailability of Drug with Low Solubility", *Chem. Biodivers.* 6(11):2071-83.
7. PCT International Application Publication No. WO 2005/074899, published Aug. 8, 2005.
8. PCT International Application Publication No. WO 2007/096588, published Aug. 30, 2007.
9. PCT International Application Publication No. WO 2010/102826, published Sep. 16, 2010.
10. Piel, G. et al. (1997) "Study of the Influence of Both Cyclodextrins and L-Lysine on the Aqueous Solubility of Nimesulide Isolation and Characterization of Nimesulide-L-Lysine-Cyclodextrin Complexes", *J. Pharm. Sci.* 86(4): 475-480.
11. Sigma Aldrich Website, "Ibuprofen Sodium Salt", retrieved Nov. 5, 2012, <www.sigmaaldrich.com/catalog/product/FLUKA/11892?lang=en&region=US>
12. U.S. Pat. No. 4,948,805, issued Aug. 14, 1990 (Ziggiotti et al).
13. U.S. Pat. No. 5,028,625, issued Jul. 2, 1991 (Motola et al).
14. U.S. Pat. No. 6,077,851, issued Jun. 20, 2000 (Bjork et al).
15. U.S. Pat. No. 6,638,537 issued Oct. 28, 2003 (Dennis et al).
16. U.S. Pat. No. 6,869,948 issued Mar. 22, 2005 (Bock et al).
17. U.S. Pat. No. 7,105,512 issued Sep. 12, 2006 (Morizono et al).
18. U.S. Pat. No. 7,589,208 issued Sep. 15, 2009 (Jannson et al).
19. U.S. Pat. No. 7,989,473 issued Aug. 2, 2011 (Patashnik et al).
20. U.S. Pat. No. 8,178,127 issued May 15, 2012 (Safadi et al).

What is claimed is:

1. Laquinimod amine salt, which is laquinimod meglumine, laquinimod choline hydroxide, laquinimod L-lysine or laquinimod monoethanolamine.

2. The laquinimod amine salt of claim 1 which is laquinimod meglumine.

3. The laquinimod meglumine of claim 2 which is isolated.

4. The laquinimod meglumine according to claim 2, wherein the laquinimod meglumine is characterized by
   a) a DSC thermogram as shown in FIGS. 4A, B and C;
   b) a solid-state $^{13}C$ NMR spectrum with broad peak at 60-77, broad peak at 122-134, peak at 142.2 and 171.3±0.2 ppm; and/or
   c) a solid state $^{13}C$ as shown in FIGS. 5A and 5B.

5. The laquinimod amine salt of claim 1 which is laquinimod choline hydroxide.

6. The laquinimod choline hydroxide of claim 5 which is isolated.

7. The laquinimod choline hydroxide according to claim 5, wherein the laquinimod choline hydroxide is characterized by
   a) a DSC thermogram as shown in FIGS. 6A, B, C, D and E;
   b) a powder XRD pattern with characteristic peaks at 10.1°, 11.8°, 13.4°, 14.4° and 16.1° 2-theta±0.2;
   c) a powder XRD pattern with characteristic peaks at 19.3°, 21.2°, 22.7°, 24.8° and 27.6° 2-theta±0.2;
   d) a powder XRD pattern as shown in FIGS. 7 and 8;
   e) a solid-state $^{13}$C NMR spectrum with peaks at about 122.1, 127.2, 142.7 and 169.7±0.2 ppm;
   f) a solid-state $^{13}$C NMR spectrum having chemical shifts differences between the signal exhibiting the lowest chemical shift in the 100 to 180 ppm range and another signal in that same chemical shift range of 100 to 180 ppm of about 12.6, 17.7, 33.2, 60.2 and ±0.1 ppm; and/or
   g) a solid state $^{13}$C NMR as shown in FIGS. 9A and B.

8. The laquinimod choline hydroxide according to any one of claims 5-7, wherein the laquinimod choline hydroxide is in crystalline form or in amorphous form.

9. The laquinimod amine salt of claim 1 which is laquinimod L-lysine.

10. The laquinimod L-lysine of claim 9 which is isolated.

11. The laquinimod L-lysine according to claim 9, wherein the laquinimod L-lysine is characterized by a) the DSC thermogram as shown in FIGS. 10A, B and C;
   b) a powder XRD pattern with characteristic peaks at 5.6°, 9.0°, 11.7°, 13.0° and 15.9° 2-theta±0.2;
   c) a powder XRD pattern with characteristic peaks at 17.9°, 18.9°, 21.1°, 22.5° and 23.0° degrees 2-theta±0.2; and/or
   d) a powder XRD pattern as shown in FIG. 11.

12. The laquinimod L-lysine according to any one of claims 9-11, wherein the laquinimod L-lysine is in crystalline form or in amorphous form.

13. The laquinimod amine salt of claim 1 which is laquinimod monoethanolamine.

14. The laquinimod monoethanolamine of claim 13 which is isolated.

15. The laquinimod monoethanolamine of claim 13, wherein the laquinimod monoethanolamine is characterized by
   a) a DSC thermogram as shown in FIG. 12A;
   b) a powder XRD pattern with characteristic peaks at 6.5°, 14.4°, 17.9°, 18.7° and 20.6° 2-theta±0.2;
   c) a powder XRD pattern with characteristic peaks at 17.1°, 19.4°, 22.3°, 23.3° and 24.8° degrees 2-theta±0.2;
   d) a powder XRD pattern as shown in FIG. 13;
   e) a DSC thermogram as shown in FIG. 12B;
   f) a powder XRD pattern with characteristic peaks at 8.2°, 9.8°, 11.2°, 13.2° and 17.9° 2-theta±0.2;
   g) a powder XRD pattern with characteristic peaks at 18.6°, 20.4°, 22.9°, 24.3° and 26.2° 2-theta±0.2; and/or
   h) a powder XRD pattern as shown in FIG. 14.

16. The laquinimod monoethanolamine according to any one of claims 13-15, wherein the laquinimod monoethanolamine is in crystalline form or in amorphous form.

17. A pharmaceutical composition comprising the laquinimod amine salt of any one of claim 1-4, 5-7, 9, 11, or 13-15 and at least one pharmaceutical acceptable excipient.

18. A process for manufacture of laquinimod amine salt according to any one of claim 1-4, 5-7, or 9-11, or 13, comprising:
   a) combining a solution of amine with laquinimod acid to form a first mixture;
   b) adding a solvent to the first mixture to form a second mixture;
   c) removing liquid from the second mixture; and
   d) recovering the laquinimod amine.

19. A process for manufacture of the pharmaceutical composition according to claim 17, comprising:
   a) obtaining laquinimod amine salt; and
   b) admixing the laquinimod amine salt with at least one pharmaceutical acceptable excipient.

20. A method for treating a subject afflicted with a form of multiple sclerosis or clinical isolated syndrome, or for alleviating a symptom of multiple sclerosis in a subject afflicted with a form of multiple sclerosis, comprising administering to the subject the pharmaceutical composition according to claim 17 so as to thereby treat the subject or alleviate the symptom of multiple sclerosis in the subject.

* * * * *